(12) United States Patent
Wheatley

(10) Patent No.: US 9,259,313 B2
(45) Date of Patent: Feb. 16, 2016

(54) HEART VALVE

(71) Applicant: David J. Wheatley, Glasgow (GB)

(72) Inventor: David J. Wheatley, Glasgow (GB)

(*) Notice: Subject to any disclaimer, the term of this patent is extended or adjusted under 35 U.S.C. 154(b) by 0 days.

(21) Appl. No.: 13/966,769

(22) Filed: Aug. 14, 2013

(65) Prior Publication Data

US 2014/0005773 A1 Jan. 2, 2014

Related U.S. Application Data

(63) Continuation of application No. PCT/GB2012/000165, filed on Feb. 17, 2012.

(30) Foreign Application Priority Data

Feb. 18, 2011 (GB) .................................. 1102828.9

(51) Int. Cl.
*A61F 2/24* (2006.01)

(52) U.S. Cl.
CPC ............ *A61F 2/2412* (2013.01); *A61F 2/2415* (2013.01); *A61F 2/2418* (2013.01); *A61F 2/2409* (2013.01); *A61F 2220/0058* (2013.01); *A61F 2230/0091* (2013.01); *A61F 2250/006* (2013.01)

(58) Field of Classification Search
CPC ... A61F 2/2412; A61F 2/2418; A61F 2/2409; A61F 2/2475; A61F 2/2415; A61F 2230/0091; A61F 2220/0058; A61F 2250/006
USPC ............ 623/2.14, 2.16, 2.17, 2.18, 1.24, 1.26
See application file for complete search history.

(56) References Cited

U.S. PATENT DOCUMENTS

| 3,197,788 A | 8/1965 | Segger | |
|---|---|---|---|
| 3,570,014 A * | 3/1971 | Hancock | 623/2.18 |
| 3,755,823 A * | 9/1973 | Hancock | 623/2.18 |
| 4,501,030 A * | 2/1985 | Lane | 623/2.18 |
| 4,605,407 A * | 8/1986 | Black et al. | 623/2.17 |
| 4,725,274 A * | 2/1988 | Lane et al. | 623/2.18 |

(Continued)

FOREIGN PATENT DOCUMENTS

| CN | 2248046 Y | 2/1997 |
|---|---|---|
| CN | 1244107 A | 2/2000 |

(Continued)

OTHER PUBLICATIONS

Hossein Ghanbari, et al., "Polymeric heart valves: new materials, emerging hopes," Cell Press, Trends in Biotechnology vol. 27 No. 6, 0167-779 (c) 2009 Elsevier Ltd., 9 pages.

(Continued)

*Primary Examiner* — Alvin Stewart
(74) *Attorney, Agent, or Firm* — Blank Rome, LLP

(57) ABSTRACT

An artificial heart valve comprises a support structure defining an aperture for blood flow and a flexible leaflet connected to the support structure along first and second at least partially straight lines of attachment, wherein the leaflet is movable relative to the support structure between an open configuration in which the leaflet permits blood flow through the aperture and a closed configuration in which the leaflet restricts blood flow through the aperture. A lateral cross-section taken through the leaflet defines an outwardly convex portion, an outwardly concave portion and a junction between the convex and concave portions. The heart valve may be configured for implantation in a human or animal subject. A method of manufacturing a heart valve and a former for use in such a method are also disclosed.

47 Claims, 13 Drawing Sheets

(56) References Cited

U.S. PATENT DOCUMENTS

| | | | |
|---|---|---|---|
| 4,851,000 A * | 7/1989 | Gupta | 623/2.18 |
| 5,330,437 A * | 7/1994 | Durman | 604/167.04 |
| 5,496,280 A * | 3/1996 | Vandenbroek et al. | 604/167.03 |
| 5,500,014 A * | 3/1996 | Quijano et al. | 623/1.24 |
| 5,562,729 A * | 10/1996 | Purdy et al. | 623/2.19 |
| 5,612,885 A * | 3/1997 | Love | 700/98 |
| 5,935,163 A * | 8/1999 | Gabbay | 623/2.14 |
| 6,264,691 B1 * | 7/2001 | Gabbay | 623/2.14 |
| 6,283,994 B1 * | 9/2001 | Moe et al. | 623/2.12 |
| 6,334,873 B1 * | 1/2002 | Lane et al. | 623/2.14 |
| 6,454,799 B1 * | 9/2002 | Schreck | 623/2.18 |
| 6,544,291 B2 * | 4/2003 | Taylor | 623/23.68 |
| 6,669,724 B2 * | 12/2003 | Park et al. | 623/1.24 |
| 6,730,118 B2 * | 5/2004 | Spenser et al. | 623/1.24 |
| 6,733,525 B2 * | 5/2004 | Pease et al. | 623/2.18 |
| 7,128,759 B2 * | 10/2006 | Osborne et al. | 623/1.24 |
| 7,160,320 B2 * | 1/2007 | Duran | 623/1.24 |
| 7,182,788 B2 * | 2/2007 | Jung et al. | 623/23.68 |
| 7,195,641 B2 * | 3/2007 | Palmaz et al. | 623/2.18 |
| 7,238,200 B2 * | 7/2007 | Lee et al. | 623/2.14 |
| 7,445,028 B1 * | 11/2008 | Aanonsen et al. | 137/846 |
| 7,744,642 B2 * | 6/2010 | Rittgers et al. | 623/1.24 |
| 8,092,518 B2 * | 1/2012 | Schreck | 623/1.26 |
| 8,092,523 B2 * | 1/2012 | Li et al. | 623/2.17 |
| 8,216,631 B2 * | 7/2012 | O'Connor et al. | 427/2.24 |
| 8,500,799 B2 * | 8/2013 | Forster et al. | 623/2.11 |
| 8,585,757 B2 * | 11/2013 | Agathos | 623/2.17 |
| 8,591,573 B2 * | 11/2013 | Barone | 623/2.1 |
| 8,628,566 B2 * | 1/2014 | Eberhardt et al. | 623/1.24 |
| 8,652,202 B2 * | 2/2014 | Alon et al. | 623/2.11 |
| 2002/0045936 A1 | 4/2002 | Moe | |
| 2002/0082687 A1 | 6/2002 | Moe | |
| 2003/0055496 A1 | 3/2003 | Cai et al. | |
| 2003/0109922 A1 * | 6/2003 | Peterson et al. | 623/2.17 |
| 2007/0208550 A1 | 9/2007 | Cao et al. | |
| 2008/0086202 A1 | 4/2008 | Lapeyre | |
| 2008/0294248 A1 * | 11/2008 | Yang et al. | 623/2.17 |
| 2009/0171432 A1 * | 7/2009 | Von Segesser et al. | 623/1.11 |
| 2010/0036504 A1 * | 2/2010 | Sobrino-Serrano et al. | 623/23.68 |
| 2010/0082094 A1 | 4/2010 | Quadri et al. | |
| 2011/0251670 A1 * | 10/2011 | Kheradvar et al. | 623/1.15 |
| 2012/0053676 A1 * | 3/2012 | Ku et al. | 623/1.26 |
| 2013/0006382 A1 * | 1/2013 | Behan | 623/23.68 |
| 2013/0304196 A1 * | 11/2013 | Kelly | 623/1.25 |
| 2014/0005773 A1 * | 1/2014 | Wheatley | 623/2.17 |

FOREIGN PATENT DOCUMENTS

| | | |
|---|---|---|
| CN | 101474102 A | 7/2009 |
| WO | 98/32400 A1 | 7/1998 |
| WO | 02100301 A1 | 12/2002 |
| WO | 2004082536 A1 | 9/2004 |
| WO | 2006108090 A2 | 10/2006 |
| WO | 2009042196 A2 | 4/2009 |

OTHER PUBLICATIONS

G. Burriesci, et al., "Design of a novel polymeric heart valve," Journal of Medical Engineering & Technology, ISSN 0309-1902 print/ISSN 1464-522X online (c) 2010 Informa UK Ltd. http://www.informaworld.com/journals DOI: 10.3109/03091900903261241, vol. 34, No. 1, Jan. 2010, 7-22.

International Search Report and Written Opinion in corresponding International Application No. PCT/GB2012/000165 dated Mar. 8, 2013.

Examination report received in corresponding New Zealand IP No. 614392 dated Mar. 7, 2014.

Office Action in counterpart Chinese Appl. 201280009575.9, dated Oct. 30, 2015.

\* cited by examiner

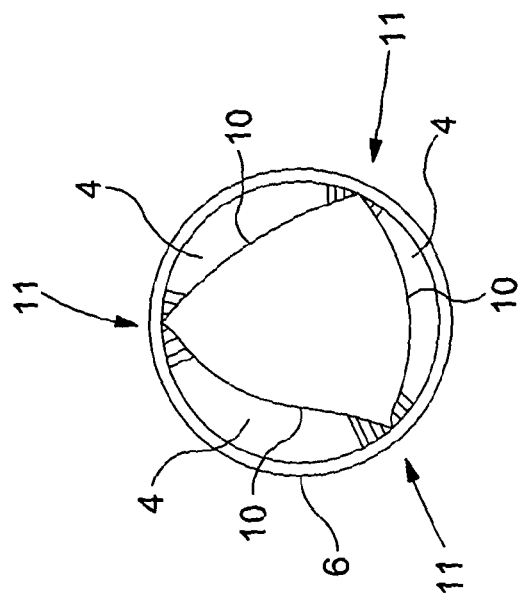
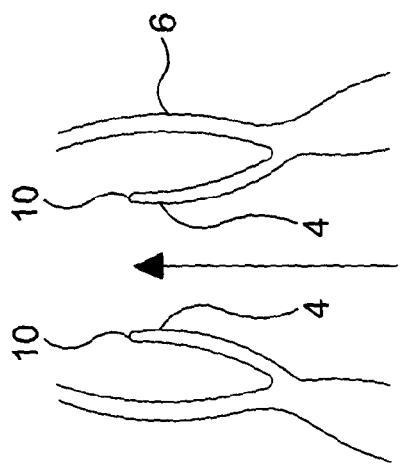
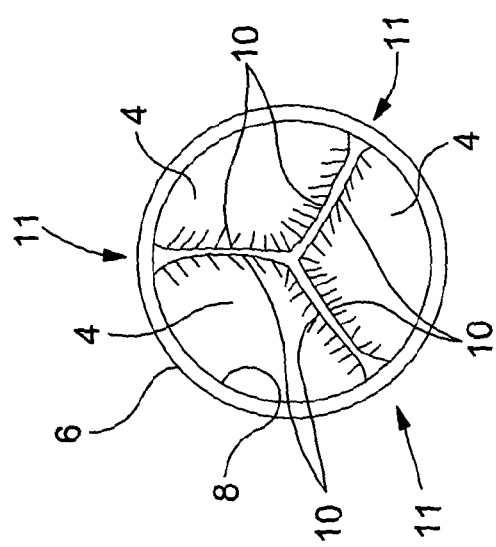
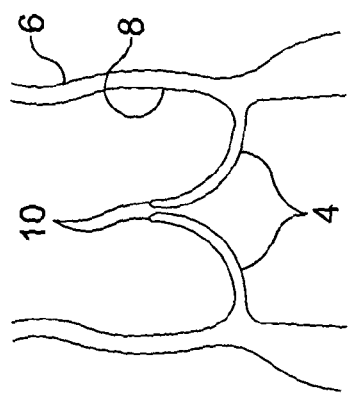
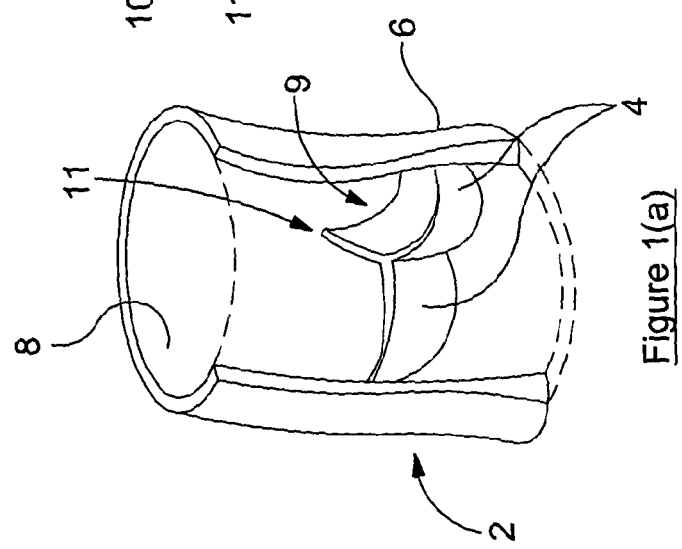

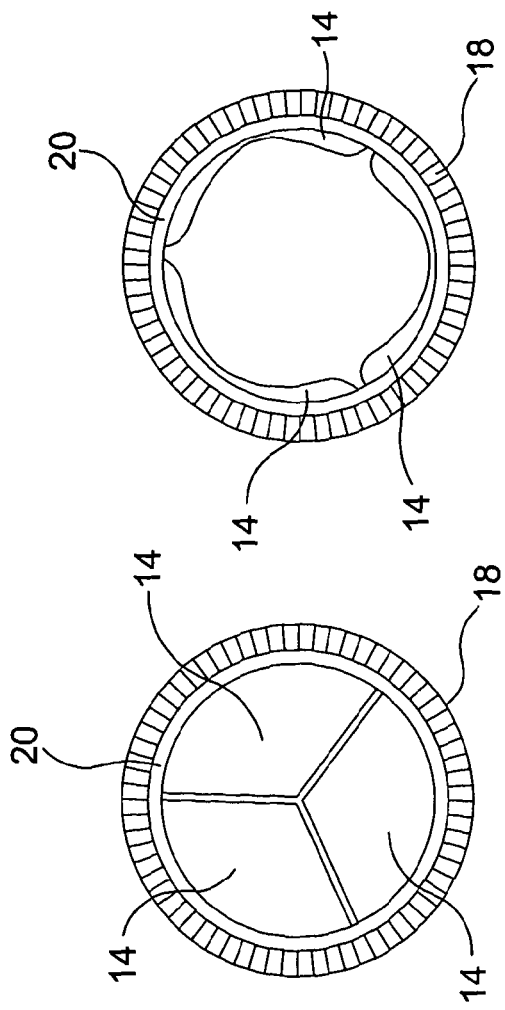
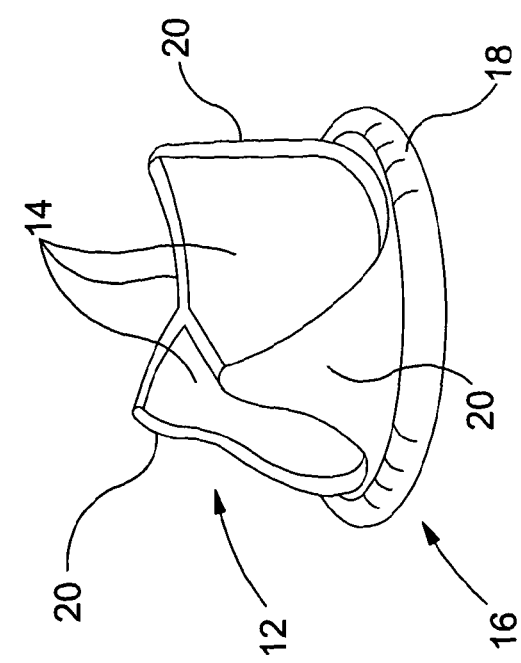
Figure 2(a)
Figure 2(b)
Figure 2(c)

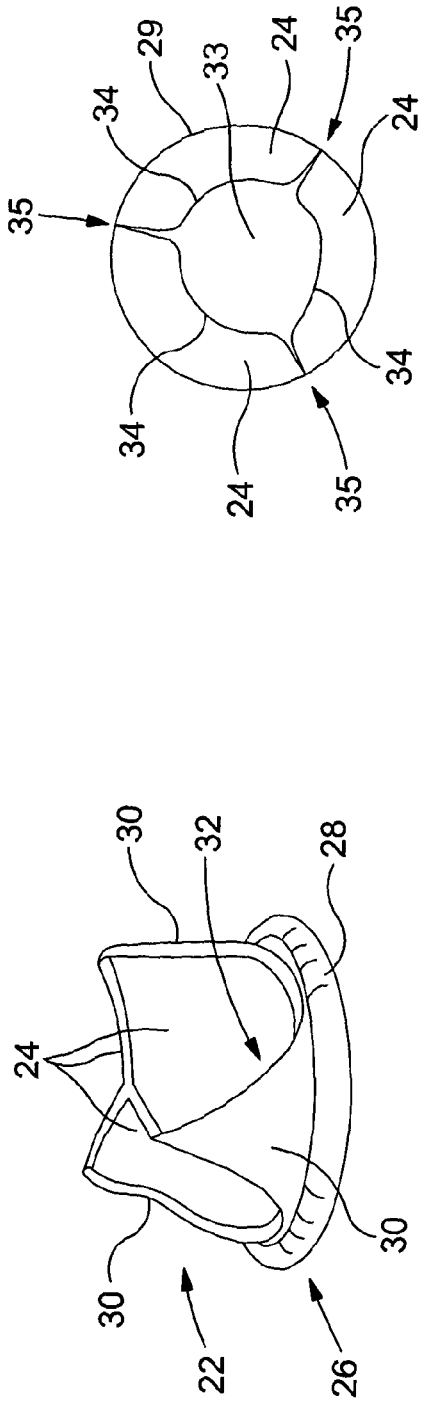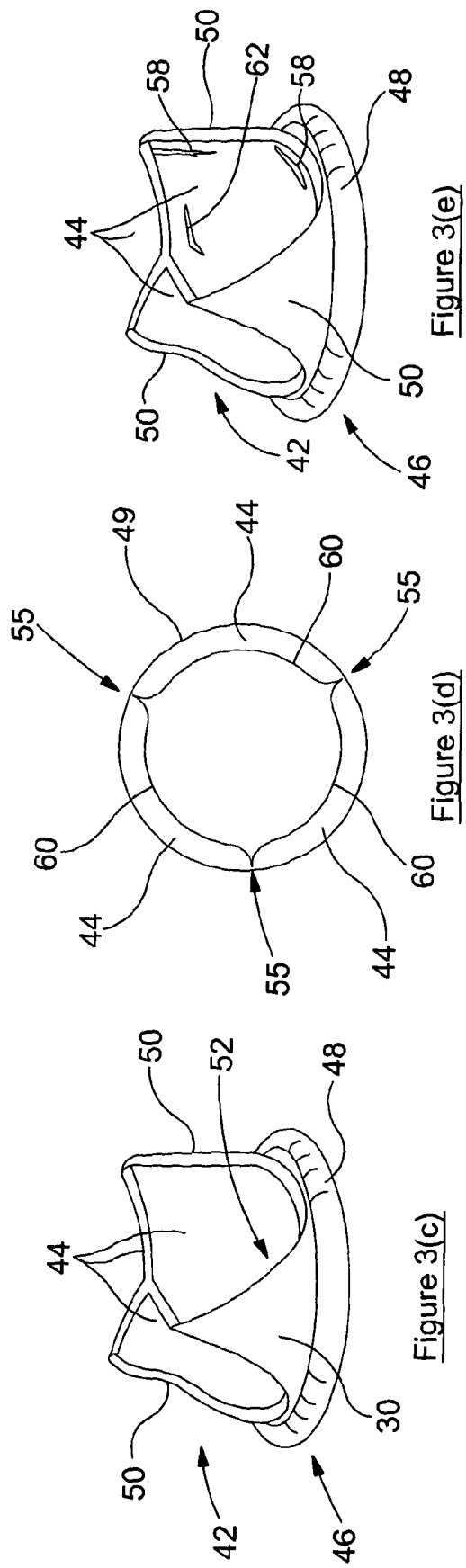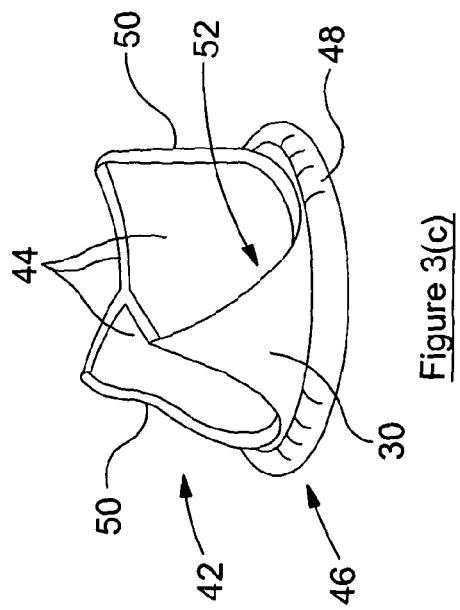

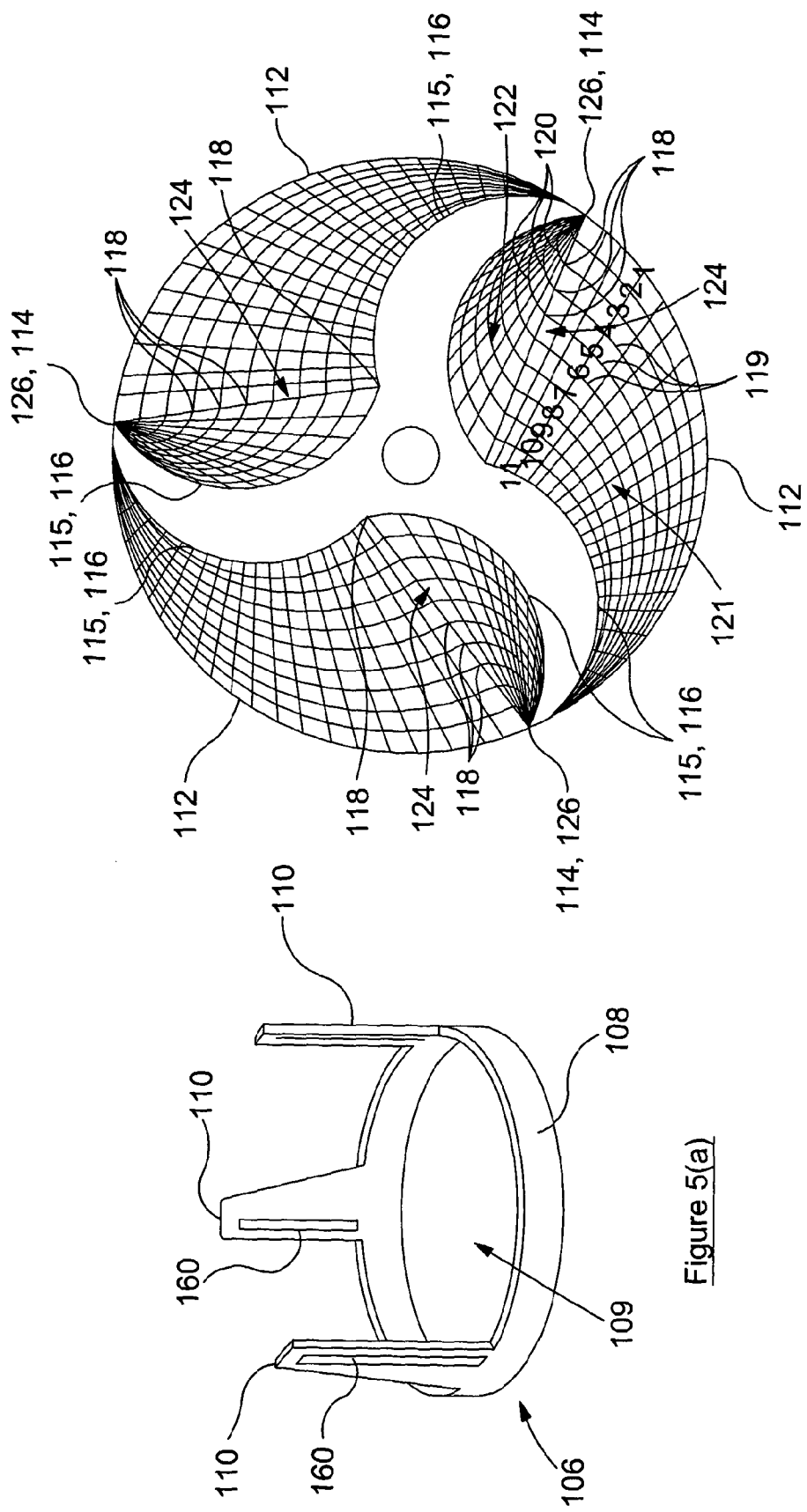

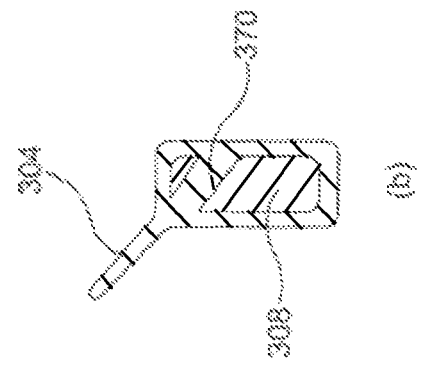
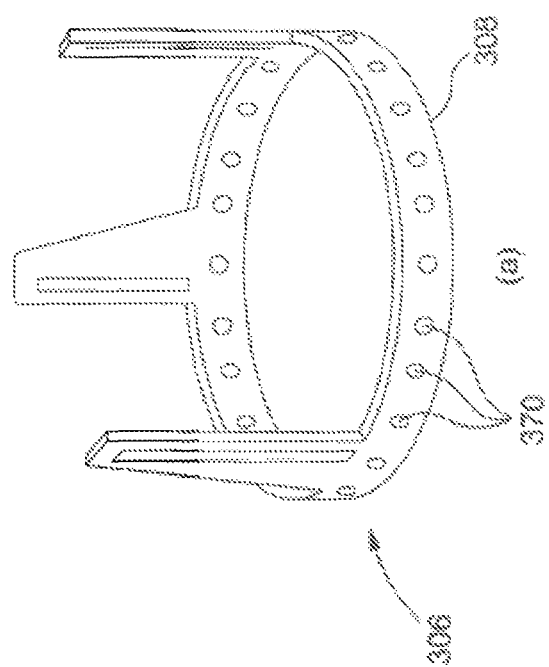
Figure 12

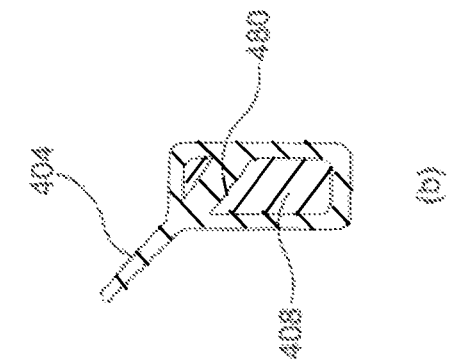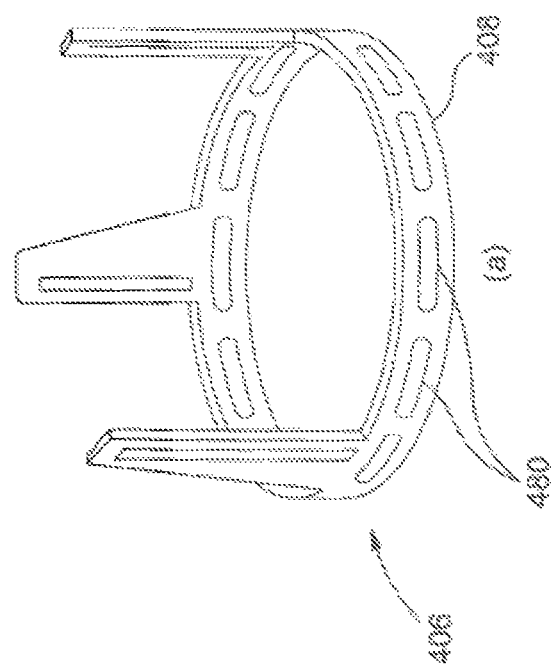
Figure 13

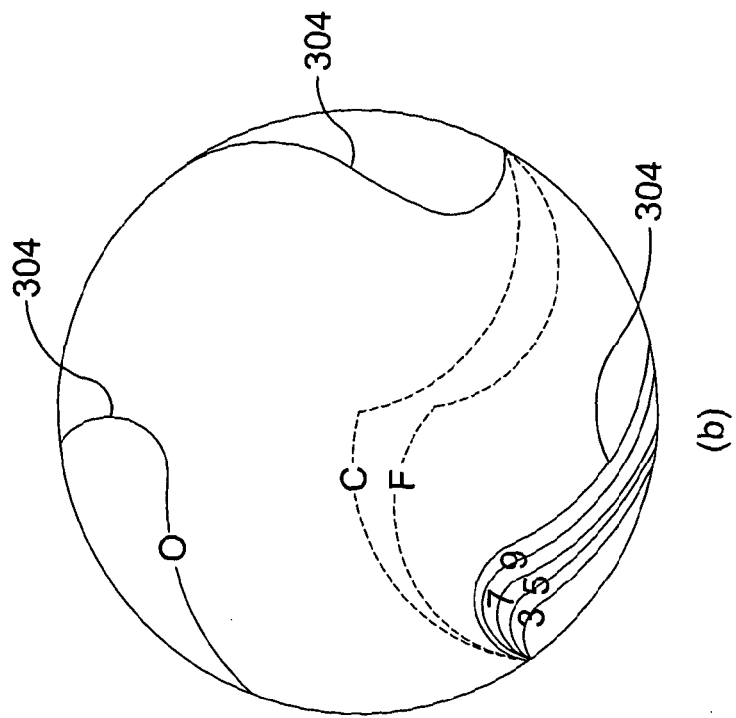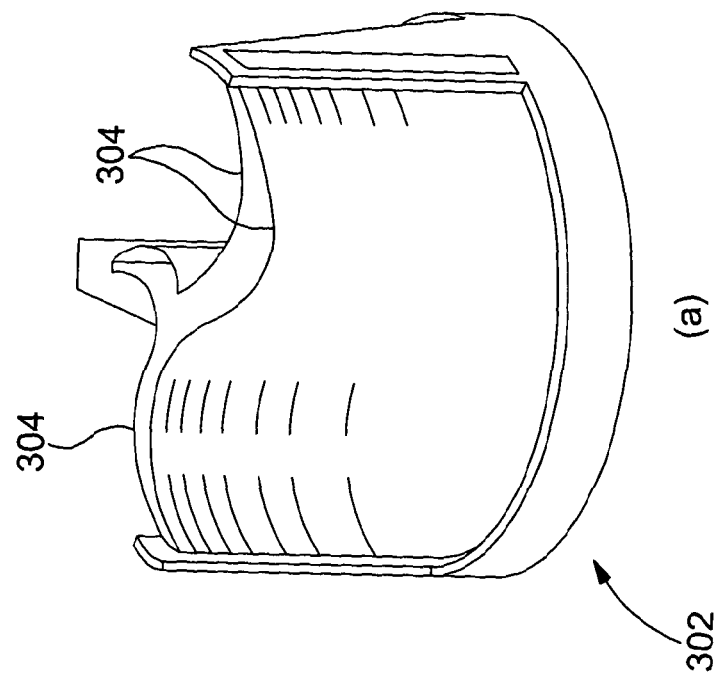
Figure 14

HEART VALVE

CROSS-REFERENCE TO RELATED APPLICATIONS

This application is a continuation of PCT Application No. PCT/GB2012/000165 filed on Feb. 17, 2012, which claims priority to United Kingdom Patent Application No. GB1102828.9 filed on Feb. 18, 2011, the contents of which are incorporated herein by reference.

FIELD OF THE INVENTION

The present invention relates to an artificial heart valve and a method of manufacturing such an artificial heart valve.

BACKGROUND OF THE INVENTION

The valves of the heart may be abnormal from birth, may become diseased, or may degenerate in old age. When their function becomes sufficiently impaired they may require to be replaced. There are many different artificial heart valves available for their replacement in established clinical use. In general, these artificial valves have been of two types. Mechanical replacement heart valves are constructed of rigid, synthetic materials such as metallic alloys, pyrolytic carbon, or rigid polymers. They do not resemble natural heart valves. Biological replacement heart valves are constructed of flexible materials of human or animal origin such as human aortic or pulmonary valves, animal aortic or venous valves, or animal pericardium (the fibrous sheet surrounding the heart). Such animal tissues are commonly treated with agents such as glutaraldehyde to enhance their durability. Biological heart valves resemble the natural aortic or pulmonary valves. Glutaraldehyde-treated bovine pericardium is a commonly used material, fashioned into three flexible leaflets on a supporting frame to mimic the natural aortic valve. These valves are implanted into the heart after removal of the abnormal valve by means of an open-heart operation. More recently, flexible valve leaflets have been attached within an expandable mesh-like cylinder for implantation via a catheter introduced into the apex of the heart or via a peripheral blood vessel. After manipulation into the correct location the device is expanded with a balloon to create a functional valve, without the need for conventional invasive surgery.

In general, mechanical valves require life-long anticoagulant drug treatment to prevent blood clotting around the valve and interfering with valve function, or spreading in the bloodstream to block vital arteries to the brain, gut, limbs or other areas, while biological valves are vulnerable to degeneration that limits their useful life, particularly in children and young adults.

Attempts to substitute a synthetic material for the biological material of the valve leaflets have been stimulated by the desire to avoid the leaflet calcification and degeneration, particularly in young adults and children, which detract from the clinical attractiveness of bioprosthetic valves. Most efforts have focussed on biostable polyurethanes. Valve design has resembled that of bioprosthetic valves in the expectation of retaining the low thrombo-embolic risk of these valves.

Synthetic polymeric, flexible-leaflet artificial heart valves, being still at an experimental stage, cannot be said to have a standard, established pattern of design. However, those examples that have been revealed in the literature mimic the design of the standard, established bioprosthetic valve, that in turn resembles the natural aortic valve of the heart. There is a good reason for this as this design retains near natural blood flow through the functioning valve. This is believed to be responsible for the bioprosthetic valve being unlikely to activate the blood clotting mechanisms of the body ("low thrombo-embolic risk"—hence allowing use of these valves without the clinical need for anticoagulation), in contrast to the "unnatural" design and abnormal flow patterns of mechanical valves.

The use of synthetic polymers, such as polyurethane, has been proposed as a possible solution to the limited durability of current flexible-leaflet bioprosthetic heart valves of animal origin. There are few examples of synthetic polymer heart valves in clinical use and these are currently confined to use in extracorporeal circuits where prolonged function is not required. Experimental polymer heart valves have shown limited durability and this is a serious disincentive to further development of such valves for clinical use as valve replacement devices. Experimental polymer heart valves have, in particular, been susceptible to damage such as tearing as a consequence of high localised bending stresses especially caused by buckling or wrinkling that may occur during valve operation.

The available polyurethanes that are suitable for medical use and that are sufficiently biostable for prolonged use in the bloodstream are relatively limited in number and are generally too stiff to allow satisfactory function of leaflets made from polyurethanes. This is particularly apparent with the stiffer, higher modulus, polyurethanes that would have greatest durability and biostability. Furthermore, the use of reinforcement within the polyurethane, such as carbon nanotubes or larger fibres, is likely to increase stiffness and render the reinforced leaflet too stiff for satisfactory haemodynamic function i.e. too stiff to allow the valve to open and close readily with satisfactory pressure drop across the valve and low regurgitation through the valve.

An important group of patients at present have no practical, satisfactory replacement heart valve available to them. This group comprises children and young adults in the developing nations. For example, Sub-Saharan Africa has the largest population of rheumatic heart disease patients in the world (World Health Organisation (WHO) estimates over 1 million aged 5-24 year olds—compared to some 33,000 in the industrialised world). Many of these go on to merit valve replacement. For these young patients the complex valve repair or valve transfer (Ross operation) procedures, sometimes applicable in the developed world, are not a feasible prospect; mechanical valves need life-long anticoagulant therapy (itself needing supervision), with a prohibitive life-long risk of bleeding or valve thrombosis; and biological valves often last only a few years before needing repeat surgery, with its own attendant risks. Thus, for the relatively small number of younger patients in the industrialised world, and for patients who cannot take anticoagulant drugs for medical or life-style reasons there is a pressing need for a durable replacement heart valve that will function clinically satisfactorily without anticoagulant drugs for many years without being vulnerable to early deterioration and failure. However, there is a very much larger population of patients in the developing world who could benefit from such a valve. Access to surgical facilities has often been a limiting factor, but with increasing development in many countries this may well become less of a problem. If a reasonably priced, reliable heart valve that did not require anticoagulation, and was easy to implant in a conventional operating room, were available, there would be a wide clinical application.

SUMMARY OF THE INVENTION

According to a first aspect of the present invention there is provided an artificial heart valve comprising a support structure defining an aperture for blood flow and a flexible leaflet connected to the support structure along first and second at least partially straight lines of attachment, wherein the leaflet is movable relative to the support structure between an open configuration in which the leaflet permits blood flow through the aperture and a closed configuration in which the leaflet restricts blood flow through the aperture, and wherein the aperture defines an axis and a lateral cross-section taken through the leaflet in a plane lateral to the axis defines an outwardly convex portion, an outwardly concave portion and a junction between the convex and concave portions.

In use, such a valve may be implanted into a human or animal such that the leaflet extends along a direction of blood flow and the lateral cross-section through the leaflet is aligned so as to be generally lateral to the direction of blood flow.

The valve may be configured for connection to a human or animal, for example, to a heart of a human or animal or to a blood vessel adjacent to a heart of a human or animal.

The valve may be configured for connection to a heart by sewing, suturing, stitching or the like.

The valve may be configured to be implanted, welded, adhered or otherwise attached to a heart.

The leaflet may be movable between the open and closed configurations in response to a change in pressure across the leaflet.

Such a heart valve may permit blood flow through the valve in a forward direction when the leaflet is in the open configuration and may restrict or prevent blood flow through the valve in a backward direction when the leaflet is in the closed configuration.

The valve may be formed so as to have a natural configuration.

The valve may be unstressed or have minimal internal stresses in the natural configuration.

The valve may have a default configuration which corresponds to the natural configuration.

The valve may be configured such that the leaflet returns to the default configuration in the absence of any pressure differential across the leaflet.

The arrangement of the leaflet in the default configuration may be intermediate the arrangement of the leaflet in the open and closed configurations.

The leaflet may have a lateral cross-section which defines an outwardly convex portion, an outwardly concave portion and a junction between the convex and concave portions in the open configuration, in the closed configuration and in all intermediate configurations between the open and closed configurations including the default configuration.

The valve may be configured to permit movement of the leaflet from the default configuration to the closed configuration in response to an appropriate pressure differential.

The valve may be configured to permit movement of the leaflet from the default configuration to the open configuration in response to an appropriate pressure differential.

The valve may be configured such that the leaflet readily moves from the default configuration to the open configuration in response to an appropriate pressure differential.

At least one of the junction, the convex portion and the concave portion may vary according to a pressure differential across the leaflet.

Straight or at least partially straight first and second lines of attachment and the configuration of the lateral cross-section through the leaflet may ensure that the leaflet is moveable between the open and closed configurations according to a preferential mode of movement in which changes in curvature of the leaflet are distributed across the whole width of the leaflet, and not primarily by changes close to the lines of attachment of the leaflet to the support structure, as is the case for many conventional designs of bioprosthetic and synthetic flexible leaflet valves. Such a mode of movement may ensure that the leaflet is moveable between the open and closed configurations whilst inducing lower bending stresses in the leaflet compared with the bending stresses induced in known artificial heart valves. For a given leaflet stiffness, this may reduce the bending stresses induced in the leaflet during operation of the heart valve and thereby reduce the susceptibility of the leaflet to damage such as tearing, cracking or the like. Thus, for a given leaflet stiffness, this may lead to improved reliability of the heart valve.

Straight or at least partially straight first and second lines of attachment and the configuration of the lateral cross-section through the leaflet may ensure that the leaflet adopts a shape which provides a reduced restriction to fluid flow when the leaflet is in the open configuration compared with known bioprosthetic heart valves or known synthetic leaflet heart valves. Consequently, such a heart valve may have improved haemodynamic performance for a given leaflet stiffness. Alternatively, for a given haemodynamic performance, such a heart valve may be constructed using a stiffer leaflet. For example, a stiffer leaflet material may be selected and/or the thickness of the leaflet may be increased without compromising haemodynamic performance relative to the haemodynamic performance of known bioprosthetic heart valves or known synthetic leaflet heart valves. This may, in particular, permit the use of stiffer higher modulus leaflet materials having greater durability and greater biostability without compromising haemodynamic performance.

Straight or at least partially straight first and second lines of attachment and the configuration of the lateral cross-section through the leaflet may ensure that the leaflet adopts a predetermined shape in response to a given pressure differential across the leaflets. More specifically, the convex and generally concave portions may vary in a predetermined manner in response to changes in pressure differential across the leaflets. This may prevent the leaflet from adopting an arbitrary shape during reconfiguration between the open and closed configurations and may, in particular, avoid acute bending, buckling or wrinkling of the leaflet during reconfiguration. For a given leaflet stiffness, this may reduce the bending stresses induced in the leaflet during operation of the heart valve and thereby reduce the susceptibility of the leaflet to damage such as tearing, cracking or the like. Thus, for a given leaflet stiffness, this may lead to improved reliability of the heart valve.

The first and second lines of attachment may be generally parallel.

The first and second lines of attachment may extend in a direction which is generally parallel to the axis.

The convex portion may extend from the first line of attachment to the junction.

The concave portion may extend from the second line of attachment to the junction.

The lateral cross-section may have a curvature which is discontinuous at the junction.

The lateral cross-section may have a curvature which is continuous at the junction.

The junction may comprise a region of inflection.

The junction may comprise a point of inflection.

The junction may comprise a curved region.

The junction may comprise a straight region.

The configuration of the lateral cross-section of the leaflet may ensure that the leaflet adopts a predetermined shape which provides improved blood flow characteristics. The configuration of the lateral cross-section of the leaflet may impart a spiral motion to the blood passing through the valve, such that the blood flow through the valve mimics physiological blood flow conditions through a natural heart valve more accurately when compared to known artificial heart valve arrangements. Such a spiral blood flow may improve the efficiency of the heart compared with the efficiency of the heart when using a known artificial heart valve.

The leaflet may be configured to define a lateral cross-section which imparts a spiral blood flow in a counter-clockwise direction when viewed from an outflow side of the valve. The lateral cross-section through the leaflet may define the outwardly convex portion followed by the outwardly concave portion in a generally counter-clockwise direction about the axis defined by the aperture when viewed from the outflow side of the valve.

The leaflet may be configured to define a lateral cross-section which imparts a spiral blood flow in a clockwise direction when viewed from the outflow side of the valve. The lateral cross-section through the leaflet may define the outwardly concave portion followed by the outwardly convex portion in a generally counter-clockwise direction about the axis defined by the aperture when viewed from the outflow side of the valve.

The artificial heart valve may be configured such that movement of the leaflet between the open and closed configurations results in the convex portion of the lateral cross-section pivoting about the first line of attachment.

The artificial heart valve may be configured such that movement of the leaflet between the open and closed configurations results in the concave portion of the lateral cross-section pivoting about the second line of attachment.

The artificial heart valve may be configured such that movement of the leaflet results in a change in curvature of the convex and concave portions of the lateral cross-section.

The artificial heart valve may be configured such that movement of the leaflet away from the closed configuration towards the open configuration results in a reduction in curvature of the convex portion of the lateral cross-section.

The artificial heart valve may be configured such that movement of the leaflet away from the closed configuration towards the open configuration results in an increase in curvature of the concave portion of the lateral cross-section.

The artificial heart valve may be configured such that movement of the leaflet from the closed configuration to the open configuration results in an initial increase in curvature of the convex and concave portions of the lateral cross-section of the leaflet followed by a decrease in curvature of the convex portion and a further increase in curvature of the concave portion.

The artificial heart valve may be configured such that movement of the leaflet results in movement of the junction along the lateral cross-section of the leaflet.

The artificial heart valve may be configured such that movement of the leaflet away from the closed configuration towards the open configuration results in movement of the junction along the lateral cross-section of the leaflet away from the first line of attachment towards the second line of attachment.

The artificial heart valve may be configured such that movement of the leaflet from the closed configuration to the open configuration results initially in no movement of the junction along the lateral cross-section of the leaflet followed by movement of the junction along the lateral cross-section of the leaflet from the first line of attachment towards the second line of attachment.

A length of the convex portion of the lateral cross-section may comprise a greater proportion of a total length of the lateral cross-section in the open configuration than in the closed configuration.

The leaflet may be connected to the support structure along a base line of attachment.

The base line of attachment may extend at least partially around the aperture.

The base line of attachment may extend circumferentially around the aperture.

The base line of attachment may be adjacent to the aperture.

The base line of attachment may be outwardly convex.

The leaflet may comprise a free edge which is movable relative to the support structure.

The free edge may extend opposite the base line of attachment between the first and second lines of attachment.

The free edge may define an outwardly convex portion, an outwardly concave portion and a junction between the convex and concave portions.

The junction of the free edge may be located substantially half-way along the free edge between the first and second lines of attachment.

The free edge of the leaflet may be longer than the base line of attachment.

Each of a plurality of lateral cross-sections taken through the leaflet between the base line of attachment and the free edge may define an outwardly convex portion, an outwardly concave portion and a junction between the convex and concave portions.

The leaflet may define a co-aptation region which extends from the free edge and which has a plurality of generally identical lateral cross-sections.

A inwardly disposed surface of such a co-aptation region may form an improved seal against a complementary inwardly disposed surface of a further co-aptation region, for example an inwardly disposed co-aptation region of a further leaflet, to prevent or reduce back flow of blood through the aperture when the leaflet is in the closed configuration.

The co-aptation region may extend from the free edge to a boundary which is located between the free edge and the base line of attachment.

A lateral cross-section which is closer to the base line of attachment but between the base line of attachment and the boundary of the co-aptation region may have a longer convex portion and a shorter concave portion than a lateral cross-section which is further from the base line of attachment but between the base line of attachment and the boundary of the co-aptation region.

The junction of each of the lateral cross-sections taken through the leaflet between the base line of attachment and the boundary of the co-aptation region may lie along a predetermined junction reference line when the leaflet is in an as-formed or natural configuration.

The junction reference line may be at least partially straight.

The junction reference line may extend from a point substantially half-way along the boundary of the co-aptation region to a point of intersection between the second line of attachment and the base line of attachment. Such an arrangement may ensure that the leaflet in its as-formed or natural configuration defines a three-dimensional generally conical region having an apex located at or adjacent the point of intersection of the second line of attachment with the base line of attachment. Such a three-dimensional leaflet shape may serve to distribute stresses across the width of the leaflet during movement of the leaflet between the open and closed configurations.

The support structure may comprise a base portion that defines the aperture.

The base portion may be curved. The base portion may comprise a loop or be generally annular. The base portion may be circular, oval or the like.

The base portion may be configured for attachment to a human or animal, for example, to a heart of a human or animal or to a blood vessel adjacent to a heart of a human or animal. The base portion may be configured to be implanted, sutured, welded, adhered or otherwise attached to a human or animal.

The aperture may be curved. The aperture may be circular, oval or the like.

The leaflet may be connected to the base portion along a base line of attachment.

The support structure may comprise a plurality of post portions extending from the base portion.

The plurality of post portions may be arranged around the aperture.

Each post portion may extend in a generally axial direction.

Each post portion may comprise a straight edge which extends in a generally axial direction. For example, the base portion may define a lateral plane and the straight edge of each post portion may extend in a direction perpendicular to the lateral plane of the base portion.

The support structure may comprise first and second post portions which define the first and second lines of attachment.

The leaflet may be attached between two post portions.

The leaflet may be attached between two adjacent post portions.

The valve may be configured such that a junction of a free edge of the leaflet lies to one side of a straight line between the two posts to which the leaflet is attached when the leaflet is in a closed configuration. The valve may be configured such that the junction of the free edge of the leaflet lies to the other side of the straight line between the two posts to which the leaflet is attached when the leaflet is in an open configuration.

Such a configuration may result in exertion of a compressive force on the leaflet as the leaflet passes between the two posts during movement of the leaflet between open and closed configurations. Such a compressive force may accentuate a curvature of the convex and concave portions of a lateral cross-section of the leaflet as the leaflet passes between the two posts.

The post portions may extend from the base portion in an outwardly splayed configuration. Each post portion may define an acute angle with respect to the axial direction. Each post portion may define an angle with respect to the axial direction of between 0 and 30°, between 0 and 10°, or between 0 and 5°. Such an outwardly splayed configuration of the post portions may permit the leaflet to move between the open and closed configurations more easily. This may reduce stress induced in the leaflet during movement thereof.

The leaflet may extend through and around the first post portion along the first line of attachment.

The leaflet may extend through and around the second post portion along the second line of attachment.

The first and second post portions may each define a hole which extends therethrough.

The leaflet may extend through the hole which extends through the first post portion along the first line of attachment.

The leaflet may extend through the hole which extends through the second post portion along the second line of attachment.

Such an arrangement may serve to provide a robust anchor between the leaflet and each of the first and second post portions.

The respective holes which extend through the first and second post portions may be angled with respect to a radial direction relative to the axis defined by the aperture. This may ensure that the leaflet enters and/or exits the respective holes which extend through the first and second post portions with a predetermined configuration such as a predetermined angle. Such an angle may ensure that a lateral cross-section of the leaflet as the leaflet emerges from the respective holes extending through the first or second post portion has a curvature which is continuous with a curvature of an outwardly convex or an outwardly concave portion of the lateral cross-section of the leaflet adjacent to the first or second post portion.

The holes which extend through the first and second post portions may each be elongated. For example, the holes which extend through the first and second post portions may each comprise a slit or the like.

The first and second post portions may each define a plurality of holes extending therethrough.

The leaflet may extend through each of the plurality of holes extending through the first and second post portions.

The leaflet may be connected to the base portion along a base line of attachment.

The leaflet may extend through and around the base portion.

The base portion may define a hole which extends therethrough.

The leaflet may extend through the hole defined by the base portion.

Such an arrangement may serve to provide a robust anchor between the leaflet and the base portion.

The one or more holes which extend through the base portion may be angled with respect to a radial direction relative to the axis defined by the aperture.

This may ensure that the leaflet enters and/or exits the one or more holes which extend through the base portion with a predetermined configuration such as a predetermined angle. Such an angle may ensure that a lateral cross-section of the leaflet as the leaflet emerges from the one or more holes extending through the base portion has a curvature which is continuous with a curvature of the leaflet adjacent to the base portion.

The one or more holes which extend through the base portion may be elongated. For example, the one or more holes which extend through the base portion may comprise slits or the like.

The base portion may define a plurality of holes extending therethrough.

The leaflet may extend through the plurality of holes defined by the base portion.

The leaflet may be integrally formed on the support structure.

The leaflet may comprise a synthetic material.

The leaflet may comprise a polymeric material.

The leaflet may comprise polyurethane.

The leaflet may comprise a composite material including a matrix material and one or more reinforcing elements. For example, the leaflet may comprise a matrix material and one or more reinforcing elements such as fibres, fibrils, strands, nanotubes or the like.

The leaflet may comprise polyurethane reinforced with carbon nanotubes.

The heart valve may comprise a plurality of flexible leaflets, each leaflet being connected to the support structure along corresponding first and second lines of attachment such that each leaflet is movable relative to the support structure between an open configuration in which the leaflet permits blood flow through the aperture and a closed configuration in which the leaflet restricts blood flow through the aperture, wherein a lateral cross-section taken through each leaflet in a plane lateral to the axis defines a corresponding outwardly convex portion, a corresponding outwardly concave portion and a corresponding junction between the convex and concave portions.

The curvature of a convex portion of a first leaflet may be substantially matched to the curvature of a concave portion of a second leaflet adjacent to the first leaflet in a lateral cross-section taken through the first and second leaflets.

Such a valve may ensure that each leaflet at least partially occludes blood flow through the valve when the leaflets are configured in the closed configuration.

Each leaflet may define a co-aptation surface which is configured to engage one or more complementary co-aptation surfaces of one or more other leaflets. Such co-aptation surfaces may form an improved seal to prevent or reduce back flow of blood through the aperture when the leaflets are in the closed configuration.

Each post portion may have a plurality of leaflets attached thereto.

Each leaflet may be integrally formed on the frame.

The valve may comprise three leaflets.

The valve may comprise three posts.

Such a valve may provide a prostheses for the ventriculo-arterial valves (aortic and pulmonary).

The valve may comprise two leaflets.

The valve may comprise two posts.

Such a valve may provide a prostheses for the atrio-ventricular valves (mitral and tricuspid).

At least a portion of the support structure may be rigid or semi-rigid.

At least a portion of the support structure may be flexible. For example, at least a portion of the support structure may be expandable.

Such a support structure may permit the valve to be compressed or collapsed for insertion into a subject's body, for example, via a blood vessel. Such a support structure may permit the valve to expand in situ over a timescale to accommodate growth of the subject.

Such a support structure may also accommodate growth of a subject such as a child.

The support structure may comprise a material which is stiffer than a material of the leaflet.

The support structure may comprise a metal.

The support structure may comprise stainless steel.

The support structure may comprise titanium.

The support structure may comprise a polymer such as polyether ether ketone (PEEK) or the like.

At least a portion of the support structure may be flexible or collapsible.

The support structure may comprise a frame.

The support structure may have a rounded profile. For example, the support structure may have rounded corners. Such a support structure should reduce the risks of injury to a human or an animal subject during deployment or implantation of the heart valve into a human or animal subject.

The valve may be configured for percutaneous delivery.

The support structure may comprise a stent.

The support structure may comprise a portion of a heart. In other words, the leaflet may be configured for direct attachment to the heart of a human or an animal.

The valve may comprise first and second inter-engageable parts.

The first part may be configured for connection to a human or animal, for example, to a heart of a human or animal or to a blood vessel adjacent to a heart of a human or animal.

The second part may comprise the leaflet. The use of such first and second parts may permit the first part to be attached to a heart without risk of damage to a leaflet of the second part.

The first part may be configured for connection to a heart by sewing, suturing, stitching or the like.

The first part may be configured to be implanted, welded, adhered or otherwise attached to a heart.

The first part may be curved. The first part may comprise a loop or be generally annular. The first part may be circular, oval or the like.

The first part may comprise a sewing ring.

The first part may be configured for connection to a heart by passing thread, wire or the like around the first part and into a wall of a heart.

The first and second parts may comprise complementary inter-engaging features.

The first and second parts may comprise male and female features.

One of the first and second parts may comprise one or more projections and the other of the first and second parts may comprise one or more recesses, wherein each recess is configured to receive a projection.

The first and second parts may be configured to provide a lockable connection with one another. For example, one of the first and second parts may comprise a bayonet and the other of the first and second parts may comprise a socket configured to receive the bayonet. The bayonet may be configured for locking within the socket by twisting the first and/or second parts relative to one another.

The support structure may comprise a third part such as an adapter part for facilitating a connection between the first and second parts.

According to a second aspect of the present invention there is provided artificial heart valve comprising a support structure defining an aperture for blood flow and a flexible leaflet connected to the support structure along first and second lines of attachment, wherein the leaflet is movable relative to the support structure between an open configuration in which the leaflet permits blood flow through the aperture and a closed configuration in which the leaflet restricts blood flow through the aperture, and wherein the aperture defines an axis and a lateral cross-section taken through the leaflet in a plane lateral to the axis defines an outwardly convex portion extending from the first line of attachment to a junction and an outwardly concave portion extending from the junction to the second line of attachment.

The first and second lines of attachment may be at least partially straight.

The first and second lines of attachment may have a generally parallel relationship.

The first and second lines of attachment may extend at least partially in a direction parallel to the axis defined by the aperture.

The first and second lines of attachment may be at least partially curved.

It should be understood that one or more of the optional features described in relation to the first aspect may apply alone or in any combination in relation to the second aspect.

According to a third aspect of the present invention there is provided artificial heart valve comprising a support structure and an integrally formed flexible leaflet, wherein the support structure defines an aperture for blood flow and a through hole and the leaflet extends through the through hole and around a portion of the support structure.

The leaflet may be integrally formed so as to extend through the through hole.

The leaflet may be integrally formed so as to extend around a portion of the support structure adjacent to the through hole.

Such an arrangement may serve to provide a robust anchor between the leaflet and the support structure.

The through hole may be elongated.

The through hole may comprise a slit or the like.

The through hole may be angled. Such a through hole may serve to ensure that the leaflet enters and/or exits the hole with a predetermined configuration such as a predetermined angle.

The support structure may define a plurality of through holes extending therethrough.

The leaflet may be integrally formed so as to extend through each of the plurality of through holes.

The leaflet may be integrally formed so as to extend around a portion of the support structure adjacent to each of the plurality of through holes.

Each of the plurality of through holes may be elongated.

Each of the plurality of through holes may comprise a slit or the like.

It should be understood that one or more of the optional features described in relation to the first aspect may apply alone or in any combination in relation to the third aspect.

According to a fourth aspect of the present invention there is provided an artificial heart valve comprising a support structure and a flexible leaflet connected to the support structure, each leaflet being formed so as to provide a predetermined shape throughout movement of the leaflet between open and closed configurations.

The leaflet may be formed so as to comprise a lateral cross-section which defines an outwardly convex portion, an outwardly concave portion and a junction between the convex and concave portions.

Such a leaflet may ensure that the convex and concave portions move in a predetermined manner in response to changes in pressure differential across the leaflet so as to avoid buckling of the leaflet.

In use, such a valve may be implanted into a human or animal subject such that the leaflet extends along a direction of blood flow and the lateral cross-section through the leaflet is aligned so as to be generally lateral to the direction of blood flow.

The heart valve may comprise a plurality of flexible leaflets, wherein each leaflet is connected to the support structure.

It should be understood that one or more of the optional features described in relation to the first aspect may apply alone or in any combination in relation to the fourth aspect.

According to a fifth aspect of the present invention there is provided a method of implanting an artificial heart valve comprising:

providing an artificial heart valve comprising a support structure defining an aperture for blood flow and a flexible leaflet connected to the support structure along first and second at least partially straight lines of attachment, wherein the leaflet is movable relative to the support structure between an open configuration in which the leaflet permits blood flow through the aperture and a closed configuration in which the leaflet restricts blood flow through the aperture, and wherein the aperture defines an axis and a lateral cross-section taken through the leaflet in a plane lateral to the axis defines an outwardly convex portion, an outwardly concave portion and a junction between the convex and concave portions; and implanting the artificial heart valve into a subject such that the axis defined by the aperture extends along a direction of blood flow.

It should be understood that one or more of the optional features described in relation to the first aspect may apply alone or in any combination in relation to the fifth aspect.

According to a sixth aspect of the present invention there is provided a leaflet for an artificial heart valve comprising first and second ends which are configured for connection to a support structure along respective first and second at least partially straight lines of attachment, the leaflet being movable between an open configuration in which the leaflet permits blood flow through an aperture of the support structure and a closed configuration in which the leaflet restricts blood flow through the aperture of the support structure, wherein a lateral cross-section taken through the leaflet in a plane extending between the ends of the leaflet defines an outwardly convex portion, an outwardly concave portion and a junction between the convex and concave portions.

It should be understood that one or more of the optional features described in relation to the first aspect may apply alone or in any combination in relation to the sixth aspect.

According to a seventh aspect of the present invention there is provided a method of manufacturing an artificial heart valve comprising:

connecting a flexible leaflet to a support structure along first and second at least partially straight lines of attachment, wherein the leaflet is movable relative to the support structure between an open configuration in which the leaflet permits blood flow through an aperture defined by the support structure and a closed configuration in which the leaflet restricts blood flow through the aperture, and wherein the aperture defines an axis and a lateral cross-section taken through the leaflet in a plane lateral to the axis defines an outwardly convex portion, an outwardly concave portion and a junction between the convex and concave portions.

The method may comprise dip-coating the support structure in a liquid.

The method may comprise permitting or causing the liquid to solidify so as to define the flexible leaflet.

The method may comprise:

mounting the support structure on a former prior to dip-coating the support structure in the liquid; and removing the support structure and the flexible leaflet from the former after solidification of the liquid.

The former may comprise an outer surface on which the liquid solidifies so as to define the flexible leaflet.

The outer surface may be configured to define the flexible leaflet of any of the heart valves of the first to fourth aspects on solidification of a liquid thereon.

The former may comprise a base portion for receiving a base portion of the support structure and a mandrel portion having the outer surface on which the liquid solidifies so as to define the flexible leaflet.

The method may comprise dipping the former with the support structure mounted thereon in the liquid so as to coat the outer surface of the former between the third edge and a lateral upper co-aptation plane located between the lateral lower co-aptation plane and the fourth edge.

The method may comprise trimming the leaflet across the co-aptation surface of the leaflet after solidification of the liquid so as to define a free edge of the leaflet.

The outer surface of the former may be configured to suppress adhesion of the liquid to the outer surface.

The liquid may comprise a molten material.

The liquid may comprise a synthetic material.

The liquid may comprise a polymeric material.

The liquid may comprise polyurethane.

The liquid may comprise a solution.

The liquid may comprise a polyurethane solution.

Such a method may ensure the integral formation and secure attachment of the leaflet to the support structure by encasing the support structure with a continuous sheet of the liquid prior to drying. This has the advantage that leaflet attachment is not limited to adhesion of the liquid material to one or more portions of the support structure thus reducing the risk of the leaflet becoming detached from the support structure, for example, during implantation or operation of the valve.

The method may comprise aligning the support structure and a former relative to one another.

The method may comprise dip-coating the support structure and the former together as an assembly in the liquid.

The method may comprise permitting or causing the liquid to solidify or dry on the former and removing the former after solidification of the liquid.

Such a former may permit the formation of the flexible leaflets and, in particular, permit the formation of the flexible leaflets having free edges which are movable relative to the support structure.

The method may comprise providing the support structure and the former with the same or corresponding alignment features to permit the support structure and the former to be aligned relative to one another. For example, the method may comprise providing the support structure and the former with complementary inter-engaging features.

The method may comprise providing the former with one alignment feature for every post portion of the support structure, and providing each post portion of the support structure with an alignment feature configured for alignment and/or engagement with a different alignment feature of the former.

The method may comprise providing each post portion of the support structure with a longitudinal aperture such as a slot, slit or the like.

The method may comprise providing each post portion of the support structure with a longitudinal recess such as a groove or the like.

The method may comprise providing the former with one longitudinal projection for each post portion of the support structure, wherein each longitudinal projection is configured for alignment or engagement with a longitudinal aperture or recess of a different post portion.

Such a method may permit a slit formed in a post portion of a support structure to be aligned with an edge of the former thus ensuring that leaflets formed on dip-coating the support structure extend around a post portion and through the slit formed therein for secure attachment thereto.

The method may comprise attaching the support structure and the former.

Such a step may ensure that a relative alignment between the support structure and the former is maintained during dip-coating.

The method may comprise providing the support structure and/or the former with the same or corresponding features to permit the support structure and the former to be attached to one another. The method may, in particular, comprise providing the support structure with a clearance hole for a locating pin or fastener such as a screw fastener and providing the former with a corresponding hole, such as a threaded hole, for receiving the locating pin or fastener.

The method may comprise injecting a release fluid through a through-hole which extends longitudinally through the former.

The method may comprise preventing liquid from solidifying or drying over a first end of the through-hole. Injecting a fluid through the through-hole may aid release of the artificial heart valve from the former once the liquid from which the leaflets are formed has solidified or dried over a second end of the release hole opposite to the first end of the through-hole.

The method may comprise injecting a liquid release fluid such as water, saline or the like through the through-hole.

The method may comprise injecting a gaseous release fluid such as air or the like through the through-hole.

The method may comprise using a syringe to inject a release fluid through the through-hole.

Such a method may result in the formation of each leaflet and the attachment thereof to the base portion along a base edge of the leaflet. Such a method may result in the formation of each leaflet such that the free edge is longer than the base edge.

Such a method may result in the formation of each leaflet such that each leaflet is attached between two post portions of a support structure.

Such a method may result in the formation of each leaflet such that each leaflet is attached to a post portion of a support structure along a side edge of the leaflet.

Such a method may result in the formation of each leaflet such that each post portion of a support structure may have a plurality of leaflets attached thereto.

The former may define a through-hole extending therethrough which is configured to receive an occluding member.

The method may comprise:

occluding the through-hole with the occluding member prior to dipping the former in the liquid so as to prevent ingress of the liquid into the through-hole;

removing the occluding member from the through-hole after solidification of the liquid; and injecting a release fluid to aid separation of the solidified liquid from the outer surface of the mandrel portion of the former It should be understood that one or more of the optional features described in relation to the first aspect may apply alone or in any combination in relation to the seventh aspect.

According to an eighth aspect of the present invention there is provided a former for use in manufacturing an artificial heart valve comprising an outer surface having first and second at least partially straight edges, wherein a lateral cross-section taken through the outer surface in a plane lateral to the first and second edges defines an outwardly convex portion, an outwardly concave portion and a junction between the convex and concave portions.

Such a former may be used for the manufacture of an artificial heart valve according to any of the first to fourth aspects of the present invention or for the manufacture of a leaflet for an artificial heart valve according to the sixth aspect, or for use in the method of manufacturing an artificial heart valve according to the seventh aspect.

The outer surface may be configured to permit solidification or drying of a liquid thereon during dip-moulding.

The outer surface may be configured to suppress adhesion of the liquid to the outer surface during dip-moulding.

The outer surface may be coated with a non-stick material.

The outer surface may be polished.

The outer surface may comprise stainless steel.

The former may be configured to receive a support structure of an artificial heart valve.

The former may be configured to permit alignment of the support structure with the former.

The former may be configured to permit attachment of the support structure to the former.

The former may comprise a base portion for receiving a base portion of the support structure and a mandrel portion comprising the outer surface on which the liquid solidifies so as to define the flexible leaflet.

The outer surface may comprise a third edge adjacent the base portion of the former and a fourth edge opposite the third edge.

Each of a plurality of lateral cross-sections taken through the outer surface of the former between the third edge and the fourth edge may define an outwardly convex portion extending from the first edge to a junction and an outwardly concave portion extending from the second edge to the junction.

The former may comprise a through-hole extending therethrough.

The through-hole may be configured to receive an occluding member to prevent ingress of the liquid into the through-hole during dip-moulding.

The through-hole may be configured to receive a release fluid to aid separation of the solidified or dried liquid from the outer surface after dip-moulding.

The through-hole may be configured to receive a liquid release fluid such as water, saline or the like.

The through-hole may be configured to receive a gaseous release fluid such as air or the like.

The through-hole may be configured to receive pressurised release fluid.

The through-hole may be configured to receive a syringe containing the release fluid.

The liquid may comprise a molten material.

The liquid may comprise a synthetic material.

The liquid may comprise a polymeric material.

The liquid may comprise polyurethane.

The liquid may comprise a solution.

The liquid may comprise a polyurethane solution.

It should be understood that one or more of the optional features described in relation to the first aspect may apply alone or in any combination in relation to the eighth aspect.

According to an ninth aspect of the present invention there is provided a method for use in implanting an artificial heart valve into a human or animal subject comprising:

sewing an attachment ring to a passageway within a human or animal subject by looping a length of suture around at least a portion of an annular base portion of the attachment ring.

The method may comprise using a continuous length of suture and repeatedly looping the suture around the annular base portion. The use of such a running suture may simplify the sewing process.

Such a method may permit the use of an attachment ring having a base portion of smaller radial extent compared with known sewing rings which have a base portion of greater radial extent to permit attachment by sewing to a passageway within a human or animal subject by passing sutures through the base portion. Using a base portion of smaller radial extent may permit use of the attachment ring with an artificial heart valve having a greater aperture for blood flow.

An outer surface of the attachment ring may be configured to sealingly engage an inner surface of the passageway.

The method may comprise holding an artificial heart valve in sealing engagement with the attachment ring so as to provide a sealed periphery around a blood flow path which extends through the attachment ring and the heart valve.

According to a tenth aspect of the present invention there is provided an attachment ring for use in implanting an artificial heart valve into a human or animal subject, the attachment ring comprising an annular base portion, wherein the attachment ring is configured to be sewn to a passageway within a human or animal subject by looping a length of suture around at least a portion of the base portion.

An outer surface of the attachment ring may be configured to sealingly engage an inner surface of the passageway.

The attachment ring may be configured to be held in engagement with an artificial heart valve so as to provide a sealed periphery around a blood flow path which extends through the heart valve and the attachment ring.

The attachment ring may be configured for engagement with the heart valve so that an inner surface of the attachment ring is held in sealing engagement with an outer surface of the heart valve.

The base portion may have a radial extent of between 0 and 3 mm, of between 0 and 2 mm, or of between 0 and 1 mm. This may permit use of the attachment ring with an artificial heart valve having a greater aperture for blood flow.

The base portion may comprise an annular support structure which is configured to prevent passage of a surgical needle therethrough during surgery. In contrast, known sewing rings comprise an annular support structure which is configured to permit passage of a surgical needle therethrough during surgery.

The support structure may comprise a metal, stainless steel, titanium, a polymer and/or polyether ether ketone (PEEK).

The attachment ring may comprise a resiliently deformable cover material which extends around at least a portion of the support structure.

The cover material may comprises Dacron.

The attachment ring may comprise an engagement feature for engaging a complementary feature of an artificial heart valve.

The attachment ring may define an aperture which defines an axial direction and the engagement feature may be configured to permit engagement with a complementary feature of an artificial heart valve along the axial direction.

The engagement feature may extend along the axial direction. This may simplify engagement of an artificial heart valve with the attachment ring during surgery, for example, within the confines of a passageway.

The engagement feature may have a non-circularly symmetric cross-section, for example a generally square or rectangular cross-section. This may ensure that engagement of the artificial heart valve and the attachment ring when in the correct relative alignment.

The engagement feature may be a female engagement feature.

The engagement feature may be a male engagement feature.

The engagement feature may be configured for locking engagement with a complementary feature of an artificial heart valve.

The engagement feature may be configured to resiliently deform on engagement with a complementary more rigid feature of an artificial heart valve.

The engagement feature may be configured to be rigid so as to cause resilient deformation of a complementary feature of an artificial heart valve on engagement therewith.

The attachment ring may comprise a plurality of engagement features for engaging a plurality of complementary features of an artificial heart valve.

According to an eleventh aspect of the present invention there is provided an artificial heart valve configured to be held in sealing engagement with the attachment ring according to the tenth aspect so as to provide a sealed periphery around a blood flow path which extends through the heart valve and the attachment ring.

According to an twelfth aspect of the present invention there is provided an artificial heart valve assembly comprising the attachment ring according to the tenth aspect in engagement with an artificial heart valve according to eleventh aspect.

BRIEF DESCRIPTION OF THE DRAWINGS

The present invention will now be described by way of non-limiting example only with reference to the following drawings of which:

FIG. 1(a) is a cut-away perspective view of a natural aortic valve with part of the aortic valve and one leaflet removed;

FIG. 1(b) is a view from an outflow side of the natural aortic valve of FIG. 1(a) in a closed configuration;

FIG. 1(c) is a longitudinal cross-section of the natural aortic valve of FIG. 1(a) in a closed configuration;

FIG. 1(d) is a view from an outflow side of the natural aortic valve of FIG. 1(a) in an open configuration;

FIG. 1(e) is a longitudinal cross-section of the natural aortic valve of FIG. 1(a) in an open configuration showing a direction of blood flow;

FIG. 2(a) is a perspective view of a pericardial bioprosthetic heart valve;

FIG. 2(b) is a view from an outflow side of the bioprosthetic heart valve of FIG. 2(a) when the valve is in a closed configuration;

FIG. 2(c) is a view from an outflow side of the bioprosthetic heart valve of FIG. 2(a) when the valve is in an open configuration;

FIG. 3(a) is a perspective view of a synthetic polymer leaflet valve having three relatively stiff leaflets and exhibiting poor haemodynamic performance;

FIG. 3(b) is a view from an outflow side of the synthetic polymer leaflet valve of FIG. 3(a) when the valve is in an open configuration wherein the valve exhibits inadequate opening;

FIG. 3(c) is a perspective view of a synthetic polymer leaflet valve having three relatively flexible leaflets and exhibiting poor durability;

FIG. 3(d) is a view from an outflow side of the synthetic polymer leaflet valve of FIG. 3(c), when the valve is in an open configuration wherein the valve exhibits high bending stresses;

FIG. 3(e) is a perspective view of the synthetic polymer leaflet valve of FIG. 3(c) showing typical locations of leaflet tears after repeated cycling in a fatigue tester;

FIG. 5(a) is a perspective view of a frame of the synthetic polymer leaflet valve of FIG. 4;

FIG. 5(b) is a contour map of the leaflets of the synthetic polymer leaflet valve of FIG. 4 viewed from an outflow side;

FIG. 12(a) is a perspective view of a first alternative frame for the synthetic polymer leaflet valve of FIG. 4;

FIG. 12(b) is a cross-section of the frame of FIG. 12(a) in a longitudinal plane in the vicinity of a base portion of the frame of FIG. 12(a) showing a leaflet extending through and surrounding the base portion;

FIG. 13(a) is a perspective view of a second alternative frame for the synthetic polymer leaflet valve of FIG. 4;

FIG. 13(b) is a cross-section of the frame of FIG. 13(a) in a longitudinal plane in the vicinity of a base portion of the frame of FIG. 13(a) showing a leaflet extending through and surrounding the base portion;

FIG. 14(a) is a perspective view of a synthetic polymer leaflet valve constituting a yet further embodiment of the present invention;

FIG. 14(b) is a partial contour map of the leaflets of the synthetic polymer leaflet valve of FIG. 14(a) in different operating configurations viewed from an outflow side;

DETAILED DESCRIPTION OF THE DRAWINGS

Figure 4:
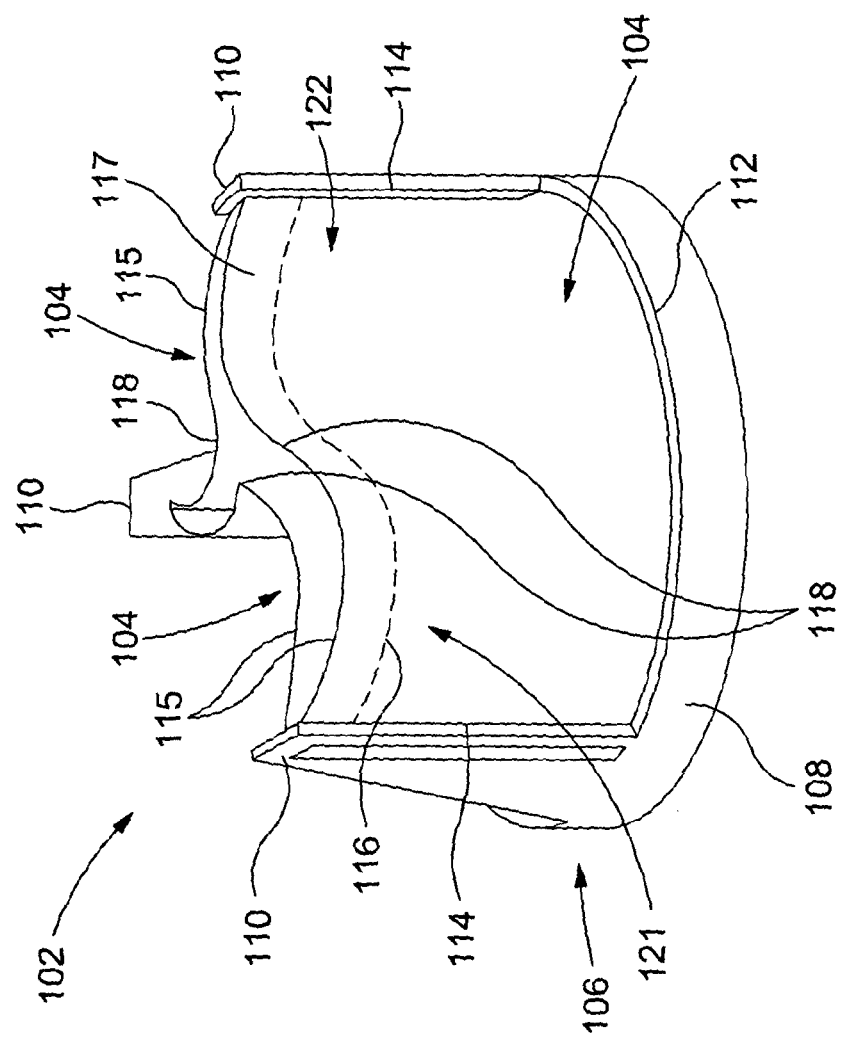
FIG. 4 is a perspective view of a synthetic polymer leaflet valve constituting an embodiment of the present invention.

With reference initially to FIG. 1(a) through 1(e), a natural aortic valve 2 comprises three pocket-like pouches or leaflets 4 of thin, flexible tissue attached circumferentially to the base or annulus of the aorta 6. The leaflets 4 are attached to an internal wall 8 of the aorta 6 along curved edges 9. Each leaflet 4 has a free edge 10 that extends in a generally lateral plane with respect to the aorta 6 and is attached to the aorta wall 8 in regions 11 known as commissures. As shown in FIGS. 1(b) and 1(c), when the valve 2 is in a closed configuration, the leaflets 4 are in apposition with one another. As illustrated in FIG. 1(b), when the valve 2 is in a closed configuration, the free edges 10 are generally convex when viewed from the outflow side. The leaflets 4 move passively in response to pressure differences on either side of the valve 2 into the open configuration shown in FIGS. 1(d) and 1(e), allowing one-way passage of blood from the left ventricle of the heart (not shown) during its contraction (emptying phase), and closing to prevent reflux of blood into the ventricle during its relaxation (filling phase).

FIG. 2(a) shows a perspective view of bioprosthetic valve 12, whilst FIGS. 2(b) and 2(c) show the same bioprosthetic valve 12 in closed and open configurations respectively. The bioprosthetic valve 12 comprises a sheet of pericardium (the fibrous sac surrounding the heart) from a donor such as a calf, with pericardial leaflets 14 mounted within (or around) a frame or stent 16 comprising an annular sewing ring base portion 18 and three projections 20 extending therefrom.

FIG. 3(a) illustrates a synthetic polymeric valve 22 comprising three relatively stiff synthetic polymeric leaflets 24 attached to a frame 26. The frame 26 comprises an annular sewing ring base portion 28 defining an inlet aperture 29 (shown in FIG. 3(b)) and three projections 30 extending therefrom. The projections 30 lie on a generally cylindrical surface which extends through the base portion 28. Furthermore, the leaflets 24 are attached to the frame 26 along respective curved lines 32 which lie on the same generally cylindrical surface as the projections 30. Such a synthetic polymeric valve 22 may, however, suffer from poor haemodynamic function as illustrated in FIG. 3(b) which shows the synthetic polymeric valve 22 in an open configuration in which the valve still presents an unacceptably high restriction to blood flow. If the polymer from which the leaflets 24 are formed is stiff, not readily distensible (high modulus), or is used to make a thick leaflet, or has some form of internal reinforcement (such as a preformed fibre network, or embedded carbon nanotubes), the leaflets 24 do not move readily in response to pressure differences across them. This results in clinically unacceptable obstruction to forward blood flow, and sluggish closure causing excessive reflux ("poor haemodynamic function"). Thus, an outlet orifice 33 formed by free edges 34 of the open leaflets 24 cannot reach the same dimensions as the inlet aperture 29. This is, in part, a consequence of the fact that a distance between adjacent commissures 35 measured around the inlet aperture 29 of the frame 26, (d/3 where d is the diameter of the inlet aperture 29), is greater than a length of a free edge 34 of one leaflet (d), and, in part, because the commissural regions of the free edges 34 adjacent to the commissures 35 cannot open to a theoretical fully open position because of the inherent stiffness of the leaflets 24. The restriction of outlet orifice area increases with increasing leaflet stiffness. Such a stiff polymer valve 22 that opens inadequately gives poor haemodynamic function and may also create areas of sluggish blood flow beneath the poorly opening leaflets 24 in the commissural regions, predisposing to local blood clotting.

FIG. 3(c) illustrates a synthetic polymeric valve 42 comprising three relatively flexible synthetic polymeric leaflets 44 attached to a frame 46. The frame 46 comprises an annular sewing ring base portion 48 defining an inlet aperture 49 (shown in FIG. 3(d)) and three projections 50 extending therefrom. The projections 50 lie on a generally cylindrical surface extending through the base portion 48. The leaflets 44 are attached to the frame 46 along respective curved lines 52 which lie on the same generally cylindrical surface as the projections 50. Such a synthetic polymeric valve 42 may provide reduced restriction when in the open configuration shown in FIG. 3(d) at the expense of reduced durability compared with the synthetic polymeric valve 22 of FIG. 3(a). If the polymer from which the leaflets 44 are made is readily distensible (low modulus), or if the leaflets 44 are very thin, the leaflets 44 will move readily in response to pressure differences across them ("good haemodynamic function"). Although such leaflets 44 offer little obstruction to forward blood flow and close readily to minimise reflux through the valve 42, durability may be limited. The valve 42 is unable to withstand the constant opening and closing stresses on the leaflets 44, and these eventually tear as illustrated in FIG. 3(e).

Features of the design of the valve 42 of FIGS. 3(c) to 3(e) may also contribute to poor durability. Full opening of the leaflets 44 requires acute bending (small radius of curvature) of the leaflets 44 in the region of commissures 55, with the result that local stresses, particularly on the commissural regions of the leaflets 44, may be very high, and may lead to the formation of tears 58 in the commissural regions of the leaflets 44 as shown in FIG. 3(e). Furthermore, during opening of the polymer leaflets 44, because the length of respective free edges 60 in their closed configuration is longer than the distance between projections 50 of the frame 46, the free edges 60 may buckle, or bend acutely and arbitrarily, as the free edges 60 pass between the projections 50, and this buckle is propagated down into the middle of each leaflet 44, causing high local bending stresses that may ultimately lead to the formation of tears 62 in the middle of the leaflets 44.

FIG. 4 shows a first embodiment of a synthetic polymeric heart valve generally designated 102 which is intended to overcome or alleviate some of the foregoing problems with known synthetic polymeric heart valves. The synthetic polymeric heart valve 102 comprises three relatively flexible polyurethane leaflets 104 attached to a relatively rigid stainless steel frame 106. The leaflets 104 are flexible relative to the frame 106 but are generally formed from a stiffer, more durable, polyurethane material than that used for polymeric leaflets of known synthetic polymeric heart valves 22, 42.

As shown in FIG. 5(a), the frame 106 comprises a generally annular base portion 108 defining an aperture 109 and three post portions 110 extending from the base portion 108 in a generally longitudinal direction. Each leaflet 104 is attached to the base portion 108 of the frame 106 along a corresponding base line of attachment 112. Each leaflet 104 is attached between two adjacent post portions 110 of the frame 106 along respective lines of attachment 114. The lines of attachment 114 are generally straight and extend in a longitudinal direction perpendicular to the base. Each leaflet 104 has a free edge 115 which extends between two adjacent post portions 110 of the frame 106 opposite the base line of attachment 112. The free edge 115 of each leaflet is free to move relative to the frame 106 in response to pressure differences on either side of the leaflets 104.

FIG. 5(b) shows a contour map of the leaflets 104 in their natural or as-formed configuration in which contour numbers 1-11 represent constant height contours increasing in distance from the base portion 108 of the frame 106 such that contour number 1 represents the base line of attachment 112 of a leaflet 104 and contour number 11 represents a lower boundary 116 of a vertical co-aptation region 117 which extends from the free edge 115 of the leaflet to the lower boundary 116 of the co-aptation region 117. From FIG. 5(b), therefore, it is apparent that a lateral section taken through each leaflet comprises a junction in the form of a point of inflection 118, an outwardly convex portion 119 extending from a first post portion 110 to the point of inflection 118 and an outwardly concave portion 120 extending from a second post portion 110 to the point of inflection 118 so that each section has an "S-shape" when viewed from the outflow direction. Accordingly, each lateral cross-section through each leaflet 104 is longer than the base line of attachment 112 of the leaflet 104. Furthermore, the free edge 115 of each leaflet 104 is longer than the corresponding base line of attachment 112. Each leaflet 104 adopts a curved shape in three dimensions which comprises an outer surface having a three-dimensional generally convex portion 121 to one side of each point of inflection 118 and a three-dimensional generally concave portion 122 to the other side of each point of inflection 118. In addition, since the lines of attachment 114 of each leaflet 104 are straight in the vicinity of each post portion 110 of the frame 106, the contour numbers 1-11 shown in FIG. 5(b) meet in the vicinity of each post portion 110 of the frame 106. The point of inflection 118 of each lateral cross-section of a leaflet 104 between the base line of attachment 112 and the lower boundary 116 of the co-aptation region 117 lies along a straight line 124 which extends from a point of intersection 126 of a line of attachment 114 adjacent to the concave portion 122 of the leaflet 104 with the base line of attachment 112 to the point of inflection 118 at the mid-point of the lower boundary 116 of the co-aptation region 117.

Figures 8, 9:
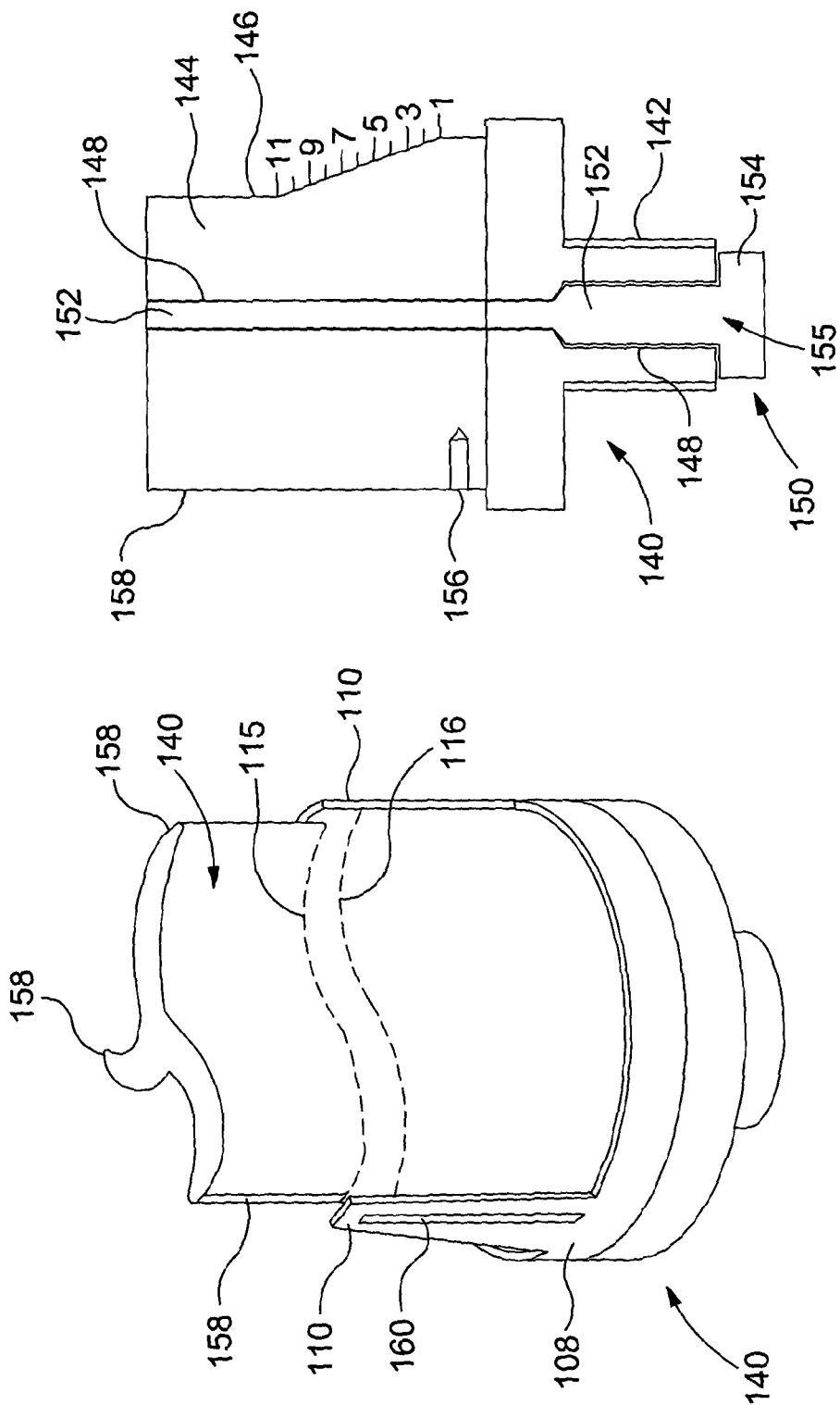
FIG. 8 is a perspective view of the valve frame of FIG. 4 positioned on a former for dip-moulding.
FIG. 9 is a longitudinal cross-section through the former shown in FIG. 8.

As will be described in more detail below, a mould or former is used to define the shape of each leaflet 104 during the manufacturing thereof. FIG. 9 shows a longitudinal cross-section through such a former showing the profile of a surface of the former to which a leaflet 104 conforms during the manufacturing thereof. Accordingly, each contour having a number 1 to 11 of the leaflets 104 is defined by a corresponding contour having a number 1 to 11 as indicated on the surface of the former in FIG. 9.

Figure 6:
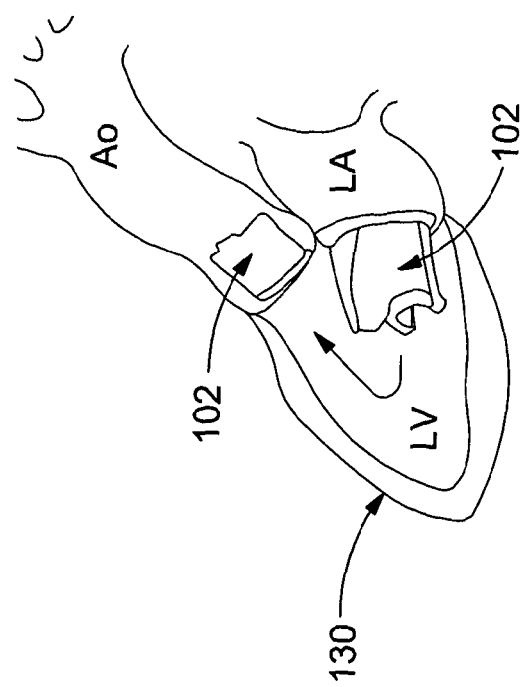
FIG. 6 is a schematic cut-away perspective view of the synthetic polymer leaflet valve of FIG. 4 in use in two different positions within the heart of a subject.

In use, the base portion 108 of the frame 106 is fitted into a circumferential sewing ring (not shown) through which surgical anchoring sutures pass to secure the artificial heart valve 102 into the attachment area (annulus) of the natural heart valve that requires replacement. As shown in FIG. 6 (in which "LA" indicates the left atrium, "LV" indicates the left ventricle, and "Ao" indicates the aorta), the artificial valve 102 is orientated in such a way as to allow appropriate one-way flow of blood through a heart 130, thus enabling it to be used to replace the aortic valve (ventriculo-arterial valve) and/or a mitral valve (atrio-ventricular valve).

Figure 7:
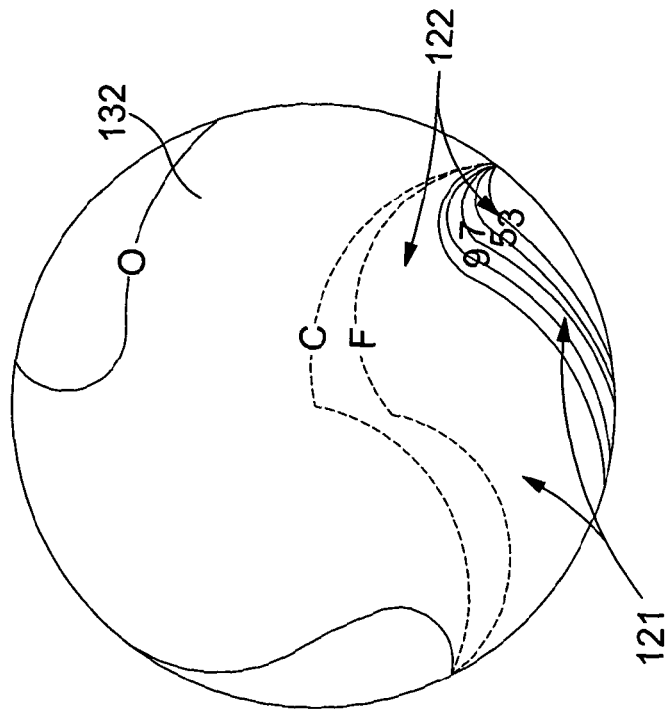
FIG. 7 is a partial contour map of the leaflets of the synthetic polymer leaflet valve of FIG. 4 in different operating configurations viewed from an outflow side.

When the valve 102 is configured in the closed configuration denoted "C" as shown dashed in FIG. 7, the free edges 115 of the flexible leaflets 104 and the inner surfaces of the co-aptation regions 117 of the leaflets 104 engage one another so as to reduce or prevent blood flow through the valve 102. When the pressure exerted on the flexible leaflets 104 from the inflow side sufficiently exceeds that exerted from the outflow side (as occurs at the commencement of ejection of blood) the leaflets 104 move outward such that the free edges 115 adopt an open configuration denoted "O" in FIG. 7 to create an outflow orifice 132, the maximum size of which can be varied by the design of the S-shape that determines the length of the leaflet free edge 115. In FIG. 7, the contour numbers 3, 5, 7 and 9 represent constant height contours of a leaflet 104 in the open configuration "O". As will be described in more detail below, the free edges 115 of the leaflets 104 are formed with a configuration denoted "F" which is intermediate the closed configuration denoted "C" and the open configuration denoted "O".

The design of the valve 102 permits use of stiffer more durable, biocompatible materials for the leaflets 104 so as to provide a reduced restriction to blood flow in the open configuration "O" compared with conventional synthetic polymer heart valves made from such stiffer materials whilst also reducing susceptibility to tearing of the leaflets 104. This improved immunity to damage is attributable not only to the increased stiffness of the leaflets 104, but also to the point of inflection defined along a lateral section through each leaflet 104. More specifically, the stiffness and the arrangement of each leaflet 104 means that, although the curvature of each leaflet 104 at a point of inflection 118 and/or the curvature of each leaflet 104 on either side of a point of inflection 118 may change in response to changes in pressure differential across the leaflets 104, the three-dimensional generally convex and concave portions 121, 122 of the leaflets 104 generally persist for different pressure differentials across the leaflets 104. As a consequence of such movement, stresses in the leaflets 104 are distributed across the widths of the leaflets 104 and the commissural regions of the leaflets 104 in the vicinity of the frame 106 do not have to bend as much as the commissural regions of leaflets of conventional synthetic heart valves (such as the leaflets 44 shown in FIGS. 3(c) to 3(e)) for a given outflow orifice size.

The stiffness and the arrangement of each leaflet 104 also means that each leaflet 104 has a predetermined shape for a given pressure differential across the leaflet 104. The predetermined shape of each leaflet 104 for a given pressure differential across the leaflet 104 is selected so as to prevent arbitrary buckling or wrinkling of each leaflet 104, thus avoiding excessive bending stresses in each leaflet 104. In particular, each leaflet 104 is formed so as to have a predetermined shape throughout movement between open and closed configurations.

With reference to FIG. 7, as each leaflet 104 moves from its closed configuration "C" towards its corresponding open configuration "O" between two adjacent post portions 110, the three-dimensional generally convex and concave portions 121, 122 of the leaflet 104 swing or pivot about their respective lines of attachment 114. The curvature of the convex and concave portions 119, 120 of the free edge 115 of the leaflet 104 are accentuated until the point of inflection 118 along the free edge 115 crosses a straight line extending between the adjacent post portions 110. Once the point of inflection 118 along the free edge 115 crosses the straight line extending between the adjacent post portions 110, the curvature of the convex portion 119 of the free edge reduces whilst the curvature of the concave portion 120 of the free edge increases and the three-dimensional generally convex portion 121 of the leaflet 104 appears to grow at the expense of the three-dimensional generally concave portion 122 of the leaflet 104 until each leaflet 104 moves reaches its corresponding open configuration "O". Corresponding changes are observed for each lateral cross-section of the leaflets 104 as defined by contours 1-11. The changes in curvature are also accompanied by movement of the points of inflection 118 along the lateral cross-sections of the leaflets 104 to accommodate the changes in curvature of the convex and concave portions 121, 122 of the leaflets 104. This results in each leaflet 104 moving continuously in a predictable manner such that the convex portion 121 of the outer surface of each leaflet 104 appears to grow at the expense of the concave portion 122 of the outer surface of the leaflet 104 when viewed from the outflow side of the valve 102. As a consequence of such movement, buckling or wrinkling of each leaflet 104 and the associated bending stresses may be avoided. This permits the valve 102 to be configured such that the bending stresses induced in each leaflet 104 as a consequence of such movement of each leaflet 104 do not exceed a threshold bending stress so that damage such as tearing of each leaflet 104 is thereby avoided.

The leaflets 104 of the three-leaflet heart valve 102 are configured to define a lateral cross-section which imparts a spiral blood flow in a counter-clockwise direction when viewed from the outflow side of the valve 102. A lateral cross-section taken through each leaflet 104 defines an outwardly convex portion 119 followed by an outwardly concave portion 120 in a generally counter-clockwise direction about an axis defined by the aperture 109 when viewed from the outflow side of the valve 102. In use, when implanted into a heart of a human or animal subject, such a spiral blood flow may improve the efficiency of operation of the heart compared with the efficiency of the heart when using known artificial heart valves.

The design of the synthetic heart valve 102 represents a significant departure from the design of a natural heart valve which has evolved naturally over millions of years and which works well for a life-time, but relies for this on the physical and biological characteristics of the complex leaflet structure, composed of collagen, elastin and glycoprotein matrix, as well as the living nature of the tissue that is able to repair and replace itself. Furthermore, the principles of design for the synthetic heart valve 102 are contrary to the principles of design employed for conventional man-made heart valve designs which dictate that such conventional man-made heart valve designs should mimic natural heart valve designs. In particular, the design of synthetic heart valve 102 differs appreciably from conventional man-made heart valve designs that mimic natural heart valve designs at least in the straight lines of attachment 114 along which each leaflet 104 is connected to post portions 110 of the frame 106. Furthermore, each lateral cross-section through each leaflet 104 defines outwardly convex and concave portions 119, 120 and a point of inflection 118 between the convex and concave portions 119, 120. A further distinguishing feature of the synthetic heart valve 102 is that each lateral cross-section through each leaflet 104 and the free edge of each leaflet 104 are both longer than the base line of attachment 112 of each leaflet 104.

FIG. 8 illustrates the manufacture of the heart valve 102 using a dip-moulding process in which the frame 106 is positioned appropriately on a former 140, dipped in a solution of polyurethane and allowed to dry in an oven. The configuration of the former 140 dictates the configuration of the valve leaflets 104 on formation. The configuration of the free edges 115 of the leaflets 104 on formation is denoted "F" in FIG. 7. In the absence of any pressure differential across the leaflets 104, the leaflets 104 tend to return to the configuration of the valve leaflets 104 on formation and, in particular, the free edges 115 of the leaflets 104 tend to return to the configuration denoted "F". This is a consequence of the properties of the material from which the leaflets are formed and is, in particular, a result of stresses induced in the material of the leaflets 104 as the leaflets 104 move away from their formation or default configuration. Moreover, the default configuration of the leaflets 104 is deliberately designed such that the free edges 115 of the leaflets 104 are not so far apart that they cannot move from their default configuration "F" to their closed configuration "C" so as to prevent blood flow in a backward direction through the valve 102 in response to an appropriate pressure differential. Furthermore, the default configuration is deliberately designed such that the free edges 115 of the leaflets 104 may readily move from their default configuration "F" to their open configuration "O" so as to minimise restriction to blood flow in a forward direction through the valve 102 in response to an appropriate pressure differential.

FIG. 9 shows the former 140 prior to mounting of the frame 106 on the former 140. The former 140 is formed from stainless steel and comprises a threaded attachment portion 142 for attachment to a support member (not shown) and a body portion 144 having a highly polished surface 146 to promote release of the artificial heart valve 102 from the former 140 after the polyurethane solution has dried. A centrally located through-hole 148 extends longitudinally through the former 140. The through-hole 148 is configured to receive an occluding pin 150 having a shank portion 152 and head portion 154. The shank portion 152 of occluding pin 150 serves to occlude the through-hole 148 so as to prevent ingress of polyurethane solution during dip-moulding into the through-hole 148. The head portion 154 of the occluding pin 150 serves to keep a region around an opening 155 of the through-hole 148 formed in the attachment portion 142 of the former 140 largely free of the polyurethane solution. The former 140 comprises a location hole 156 configured for alignment and attachment of the frame 106 to the former 140 using a locating pin (not shown) to prevent relative movement therebetween during the dip-moulding process. This ensures that each side edge 158 of the former is aligned adjacent to a corresponding post portion 110 of the frame 106.

After dip-moulding, the occluding and locating pins 154, 156 are removed from the former 140. Subsequently, the release of the artificial heart valve 102 from the former 140 may be aided by injecting a release fluid such as water or saline into the opening 155 of the through-hole so as to induce planar separation of the leaflets 104 from the highly polished surface 146 of the body portion 144 of the former 140. It should be understood that the former is dipped in the polyurethane solution such that the polyurethane solution solidifies to a level above the lower boundaries 116 of the co-aptation regions 117 defined by contour 11 on the former 140. The leaflets 104 may be subsequently trimmed at a level above contour 11 so as to form the free edges 115 and define a height of the co-aptation regions 117 from the lower boundaries 116 of the co-aptation regions 117 to the free edges 115.

Figure 10B:
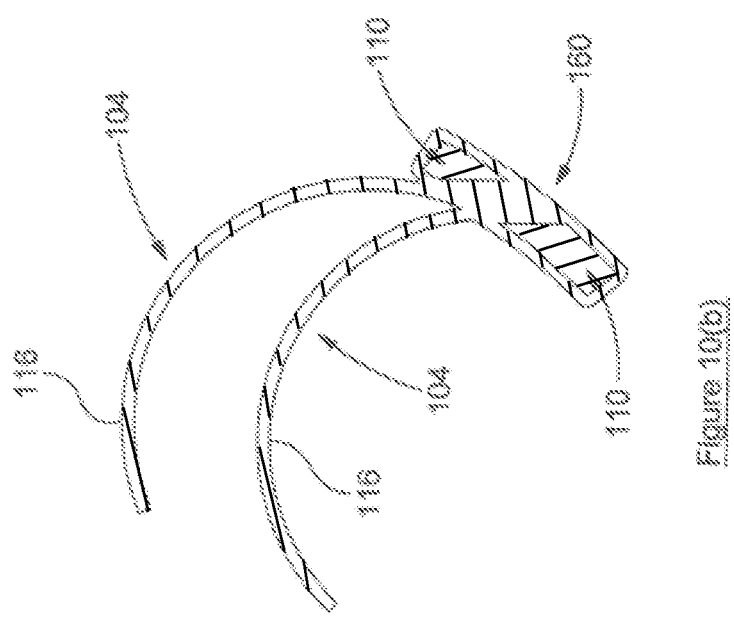
FIG. 10(b) is a cross-section of the valve of FIG. 4 in a lateral plane of the valve in the vicinity of a post portion of the frame showing integrally formed adjacent leaflets surrounding the post portion and passing through a slit in the post portion.
Figure 10A:
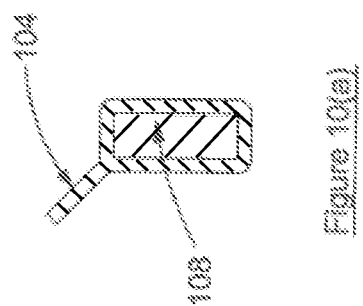
FIG. 10(a) is a cross-section of the valve of FIG. 4 in a longitudinal plane of the valve in the vicinity of a base portion of a frame of the valve showing a leaflet surrounding the base portion.

The dip-moulding process allows the polymer to surround the frame 106 including the base portion 108 as shown in FIG. 10(a) and to pass through slits 160 in the post portions 110 of the frame 106 as shown in FIG. 10(b) so as to completely envelope the frame 106 and ensure integral formation of the leaflets 104 and secure attachment of the leaflets 104 to the frame 106. Such a manufacturing process may ensure the integral formation and secure attachment of the leaflets 104 to the frame 106 by encasing the frame 106 with a continuous sheet of the polyurethane. This has the advantage that leaflet attachment is not limited to adhesion of the polyurethane to one or more portions of the frame 106 thus reducing the risk of the leaflets 104 becoming detached from the frame 106. Furthermore, the slits 160 are angled so as to ensure that the leaflets 104 enter and/or exit the slits 160 with a predetermined configuration. Such an angle may, in particular, ensure that the curvature of a lateral cross-section of the leaflets 104 in the vicinity of the post portions 110 is continuous with a curvature of the convex and concave portions 119, 120 of the lateral cross-section of the leaflets 104.

Figure 11:
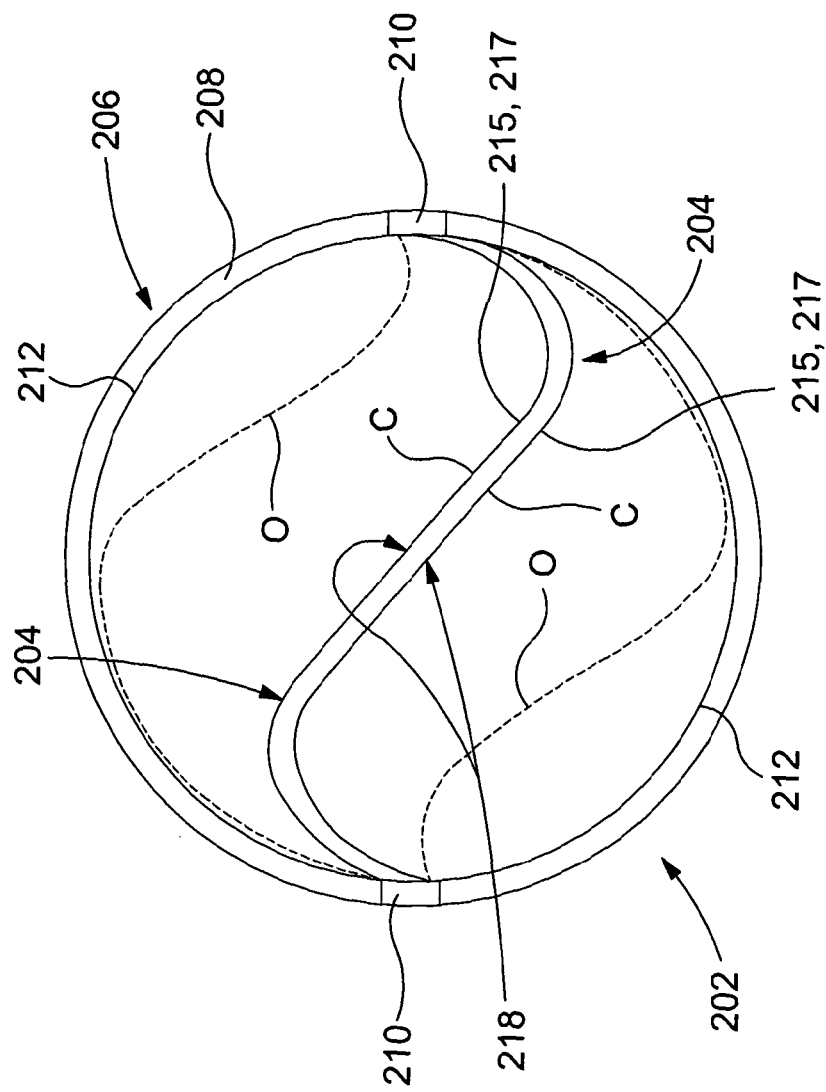
FIG. 11 is a view from an outflow side of a bi-leaflet valve constituting a further embodiment of the present invention showing a closed configuration (solid line) and an open configuration (dashed line) of the valve leaflets.

FIG. 11 shows a second embodiment of a synthetic polymeric heart valve generally designated 202 comprising two flexible leaflets 204 attached to a frame 206 along two generally straight lines of attachment defined by respective post portions 210 extending from a base portion 208 which defines an aperture for blood flow. Each leaflet 204 is attached to the base portion 208 of the frame 206 along a base line of attachment 212. Each leaflet 204 extends along a direction of blood flow to a free edge 215 which is movable from a closed configuration denoted "C" in FIG. 11 to an open configuration denoted "O" and shown dashed in FIG. 11. The leaflets 204 of the bi-leaflet heart valve 202 are configured to define a lateral cross-section which imparts a spiral blood flow in a clockwise direction when viewed from the outflow side of the valve 202. A lateral cross-section through each leaflet 204 defines an outwardly concave portion followed by an outwardly convex portion in a generally counter-clockwise direction about an axis defined by the base portion 208 when viewed from the outflow side of the valve. In other respects, the bi-leaflet heart valve 202 is designed using the same design principles outlined above for the three-leaflet synthetic polymeric heart valve 102 and operates in a like manner.

One skilled in the art will understand that various modifications may be made to the forgoing embodiments without departing from the scope of the present invention. For example, FIG. 12(a) shows a perspective view of a first alternative frame 306 for the synthetic polymer leaflet valve of FIG. 4 comprising a base portion 308 and a plurality of through-holes 370 extending through the base portion 308. FIG. 12(b) is a cross-section of the frame of FIG. 12(a) in a longitudinal plane in the vicinity of the base portion 308 which shows a leaflet 304 extending through a through-hole 170 and surrounding the base portion 308. Each of the through-holes 370 are angled upwardly by approximately 30° to the horizontal so as to ensure that a curvature of the leaflet 304 adjacent to the base portion 308 is continuous with a curvature of convex and concave portions 321, 322 of the leaflets 304.

FIG. 13(a) shows a perspective view of a second alternative frame 406 for the synthetic polymer leaflet valve of FIG. 4 comprising a base portion 408 and a plurality of slits 480, each slit 480 extending through the base portion 408. FIG. 13(b) is a cross-section of the frame of FIG. 13(a) in a longitudinal plane in the vicinity of the base portion 408 which shows a leaflet 404 extending through a slit 480 and surrounding the base portion 408. Each of the slits 480 are angled upwardly by approximately 30° to the horizontal so as to ensure that a curvature of the leaflet 404 adjacent to the base portion 408 is continuous with a curvature of convex and concave portions 421, 422 of the leaflets 404.

In further alternative frames (not shown) for the synthetic polymer leaflet valve of FIG. 4, instead of having slits for the attachment of the leaflets to the post portions of the frame along the generally straight lines of attachment, the post portions may each define a plurality of through holes aligned along the post portions for the attachment of leaflets along generally straight lines of attachment.

Rather than being rigid or semi-rigid, the frame 106 may be flexible. For example, the frame 106 may be expandable to permit the valve 102, 202 to enlarge with natural growth in a growing subject such as a child, or to be forcibly expanded by a balloon or other method, without making the valve leaflets 104, 204 incompetent and leaking. Apposition of the leaflets 104, 204 at the co-aptation regions 117, 217 is maintained by alteration of the curvature of the leaflets as the post portions 110, 210 move apart with enlargement of the valve 102, 202.

It should be understood that, in some embodiments, one or more leaflets may be configured to define a lateral cross-section which imparts a spiral blood flow in a counter-clockwise direction when viewed from an outflow side of the valve. A lateral cross-section through each leaflet may define an outwardly convex portion followed by an outwardly concave portion in a generally counter-clockwise direction about an axis defined by the aperture when viewed from the outflow side of the valve. For example, the three leaflet heart valve 102 shown in FIGS. 4, 5(b), 7 and 8 is configured such that the leaflets 104 define a lateral cross-section which imparts a spiral blood flow in a counter-clockwise direction when viewed from the outflow side of the valve 102.

In other embodiments, one or more leaflets may be configured to define a lateral cross-section which imparts a spiral blood flow in a clockwise direction when viewed from the outflow side of the valve. A lateral cross-section through each leaflet may define an outwardly concave portion followed by an outwardly convex portion in a generally counter-clockwise direction about the axis defined by the aperture when viewed from the outflow side of the valve. For example, the two leaflet heart valve 202 of FIG. 11 is configured such that the leaflets 204 define a lateral cross-section which imparts a spiral blood flow in a clockwise direction when viewed from the outflow side of the valve 202. Similarly, FIGS. 14(a) and 14(b) show a three leaflet heart valve 302 which is configured such that the leaflets 304 define a lateral cross-section which imparts a spiral blood flow in a clockwise direction when viewed from the outflow side of the valve 302.

Figure 15:
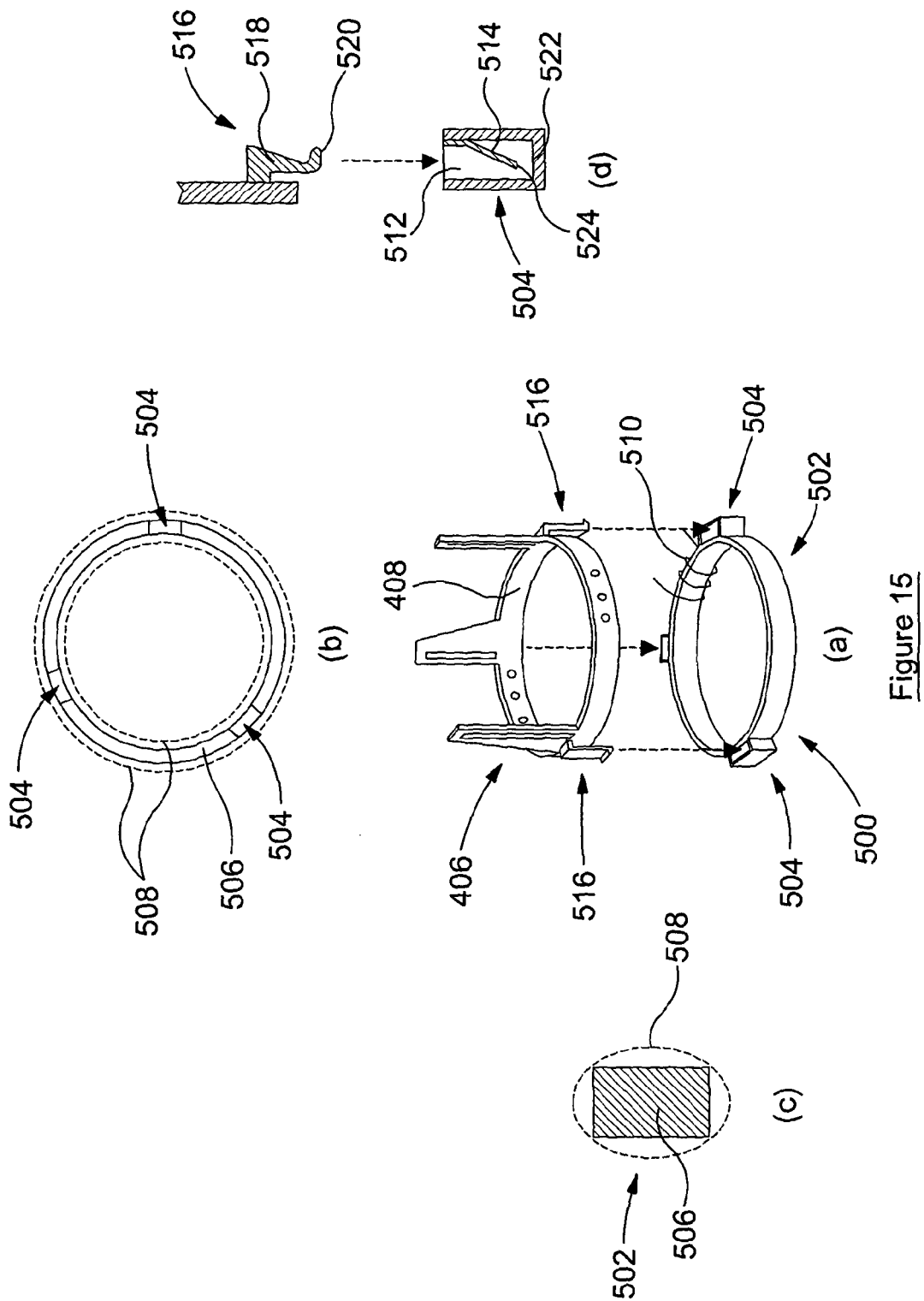
FIG. 15(a) is a schematic perspective view showing the assembly of a frame of an artificial heart valve and an attachment ring.
FIG. 15(b) is a schematic plan view of the attachment ring of FIG. 15(a)
FIG. 15(c) is a schematic cross-section through a base portion of the attachment ring of FIG. 15(a)
FIG. 15(d) is a schematic cross-section through a base portion of the attachment ring of FIG. 15(a) in the vicinity of a female engagement feature of the attachment ring.

Referring to FIG. 15(a) there is shown a schematic perspective view illustrating the assembly of a frame 406 of an artificial heart valve and an attachment ring generally designated 500. Referring to FIGS. 15(a) and 15(b), the attachment ring 500 comprises an annular base portion 502 which defines three female engaging features in the form of three receptacles 504 which are distributed circumferentially around the base portion 502. As shown most clearly in the cross-sectional view through the base portion 502 of FIG. 15(c), the base portion 502 comprises an annular support structure 506 surrounded by a resiliently deformable cover material in the form of a Dacron layer 508. In use, a running suture 510 is used to sew the base portion 502 to a passageway (not shown) within the heart of a human or animal subject by looping a continuous length of suture repeatedly around the base portion 502. The Dacron layer 508 is then compressed against an inner surface of the passageway (not shown) to provide a seal therewith around an outer surface of the base portion 502. The suture 510 sinks into the Dacron layer 508 so as to avoid interfering with the seal between the outer surface of the base portion 502 and the inner surface of the passageway (not shown) and so as to avoid interfering with a subsequent seal formed between an inner surface of the base portion 502 and an outer surface of an annular base portion 408 of the frame 406. Such a sewing method may permit the use of an attachment ring 500 having an annular base portion 502 which has a radial extent which is substantially less than the radial extent of known sewing rings. This may permit the use of artificial heart valves which define greater blood flow apertures.

As shown in FIG. 15(d) each receptacle 504 comprises a recess 512 and a resiliently deformable member 514 which extends downwardly and across the recess 512. The recess 512 has a generally rectangular cross-section. The frame 406 of the artificial heart valve comprises three rigid male engaging features in the form of three bayonets 516 each having corresponding leg and foot portions 518, 520. Each bayonet 516 has a generally rectangular cross-section which is configured to be received within a corresponding recess 512. During assembly, each bayonet 516 is aligned with and pushed into a corresponding recess 512 so that the foot portion 520 of the bayonet first engages and then deforms a corresponding deformable member 514 When the foot portion 520 is pushed fully into the recess 512, the foot portion 520 engages a closed end 522 of the recess 512 thus permitting a lower end 524 of the deformable member 514 to spring back to its natural position and thereby lock the corresponding bayonet 516 in engagement within the recess 512. Such a push fit arrangement may simplify the attachment of the frame 406 of an artificial heart valve to a passageway (not shown) within the heart of a human or animal subject.

The invention claimed is:

1. An artificial heart valve comprising a support structure defining an aperture for blood flow and a flexible leaflet which is movable relative to the support structure between an open configuration in which the leaflet permits blood flow through the aperture and a closed configuration in which the leaflet restricts blood flow through the aperture, wherein the aperture defines an axis and a lateral cross-section taken through the leaflet in a plane lateral to the axis defines an outwardly convex portion, an outwardly concave portion and a junction between the convex and concave portions when the leaflet is in the open and closed configurations and all leaflet configurations intermediate the open and closed configurations including a natural or default configuration in which the leaflet is formed, and wherein the leaflet is attached to the support structure along first and second at least partially straight lines of attachment such that movement of the leaflet between the open and closed configurations results in the convex portion of the lateral cross-section pivoting about one of the first and second lines of attachment and the concave portion of the lateral cross-section pivoting about the other of the first and second lines of attachment.

2. An artificial heart valve according to claim 1, wherein the first and second lines of attachment extend in a direction which is generally parallel to the axis.

3. An artificial heart valve according to claim 1, wherein the convex portion extends from one of the first and second lines of attachment to the junction and the concave portion extends from the other of the first and second lines of attachment to the junction.

4. An artificial heart valve according to claim 1, wherein movement of the leaflet from the closed configuration to the open configuration results in an initial increase in curvature of the convex and concave portions of the lateral cross-section of the leaflet followed by a decrease in curvature of the convex portion and a further increase in curvature of the concave portion.

5. An artificial heart valve according to claim 1, wherein the heart valve is configured such that movement of the leaflet results in movement of the junction along the lateral cross-section of the leaflet.

6. An artificial heart valve according to claim 1, wherein movement of the leaflet from the closed configuration to the open configuration results initially in no movement of the junction along the lateral cross-section of the leaflet followed by movement of the junction along the lateral cross-section of the leaflet from the first or second line of attachment about which the convex portion pivots towards the other of the first and second lines of attachment.

7. An artificial heart valve according to claim 1, comprising one or more further flexible leaflets, wherein each of the one or more further leaflets is movable relative to the support structure between an open configuration in which the leaflet and the one or more further leaflets permit blood flow through the aperture and a closed configuration in which the leaflet and the one or more further leaflets restrict blood flow through the aperture, wherein a lateral cross-section taken through any one of the one or more further leaflets in a plane lateral to the axis defines a corresponding outwardly convex portion, a corresponding outwardly concave portion and a corresponding junction between the convex and concave portions when said further leaflet is in the open and closed configurations and all leaflet configurations intermediate the open and closed configurations including a natural or default configuration in which the further leaflet is formed, and wherein each of the one or more further leaflets is attached to the support structure along respective at least partially straight first and second lines of attachment such that movement of any one of the one or more further leaflets between a corresponding open and closed configuration results in the convex portion of the lateral cross-section of the further leaflet pivoting about one of the corresponding first and second lines of attachment and the concave portion of the lateral cross-section of the further leaflet pivoting about the other of the corresponding first and second lines of attachment.

8. An artificial heart valve according to claim 1, wherein a curvature of the convex portion of the lateral cross-section of the leaflet is substantially matched to a curvature of a concave portion of a lateral cross-section of one of the one or more further leaflets adjacent to the leaflet, wherein said lateral cross-sections are taken through the leaflet and the adjacent further leaflet in the same plane lateral to the axis.

9. An artificial heart valve according to claim 1, wherein the support structure comprises a through hole and the leaflet is integrally formed so as to extend through the through hole and surround a portion of the support structure.

10. An artificial heart valve according to claim 9, wherein the through hole is elongated.

11. An artificial heart valve according to claim 9, wherein the through hole comprises a slit.

12. An artificial heart valve according to claim 9, wherein the through hole is angled with respect to a radial direction defined relative to an axis defined by the aperture.

13. An artificial heart valve according to claim 9, wherein through hole is defined in a post portion of the support structure.

14. An artificial heart, valve according to claim 9, wherein through hole is defined in a base portion of the support structure.

15. An artificial heart valve according to claim 9, wherein the support structure defines a plurality of through holes extending therethrough and the leaflet is integrally formed so as to extend through each of the through holes.

16. An artificial heart valve according to claim 15, wherein the leaflet is integrally formed so as to surround a portion of the support structure adjacent to each through hole.

17. An artificial heart valve according to claim 1, wherein the leaflet is attached to the support structure along a base line of attachment which is adjacent to the aperture.

18. An artificial heart valve according to claim 17, wherein the leaflet comprises a free edge which extends opposite the base line of attachment and which extends between the first and second lines of attachment, the free edge being movable relative to the support structure, and the free edge defining an outwardly convex portion, an outwardly concave portion and a junction between the convex and concave portions.

19. An artificial heart valve according to claim 18, wherein the free edge of the leaflet is longer than the base line of attachment.

20. An artificial heart valve according to claim 18, wherein each of a plurality of lateral cross-sections taken through the leaflet between the base line of attachment and the free edge defines an outwardly convex portion, an outwardly concave portion and a junction between the convex and concave portions.

21. An artificial heart valve according to claim 18, wherein the leaflet defines a co-aptation region which extends from the free edge to a boundary which is located between the free edge and the base line of attachment, the co-optation region defining a plurality of generally identical lateral cross-sections.

22. An artificial heart valve according to claim 21, wherein the lateral cross-section is located axially between the base line of attachment and the boundary of the co-aptation region, wherein the leaflet defines a further lateral cross-section which is taken through the leaflet in a further plane which is lateral to the axis and which is located axially between the base line of attachment and the boundary of the co-aptation region at an axial position which is further from the base line of attachment than the axial position of the lateral cross-section, wherein the further lateral cross-section defines a further outwardly convex portion, a further outwardly concave portion and a further junction between the further convex portion and the further concave portion, and herein the convex portion of the lateral cross-section is longer than the further convex portion of the further lateral cross-section and the concave portion of the lateral cross-section is shorter than the further concave portion of the further lateral cross-section.

23. An artificial heart valve according to claim 17, wherein the base line of attachment is outwardly convex.

24. An artificial heart valve according to claim 17, wherein the entire base line of attachment extends circumferentially at least part way around the aperture.

25. An artificial heart valve according to claim 1, wherein a length of the convex portion of the lateral cross-section comprises a greater proportion of a total length of the lateral cross-section in the open configuration than in the closed configuration.

26. An artificial heart valve comprising a support structure defining an aperture for blood flow and a flexible leaflet which is movable relative to the support structure between an open configuration in which the leaflet permits blood flow through the aperture and a closed configuration in which the leaflet restricts blood flow through the aperture,
   wherein the aperture defines an axis and a lateral cross-section taken through the leaflet in a plane lateral to the axis defines an outwardly convex portion, an outwardly concave portion and a junction between the convex and concave portions,
   wherein the leaflet is attached to the support structure along first and second at least partially straight lines of attachment such that movement of the leaflet between the open and closed configurations results in the convex portion of the lateral cross-section pivoting about one of the first and second lines of attachment and the concave portion of the lateral cross-section pivoting about the other of the first and second lines of attachment, and
   wherein the leaflet is attached to the support structure along a base line of attachment which is adjacent to the aperture and which is outwardly convex.

27. An artificial heart valve comprising a support structure defining an aperture for blood flow and a flexible leaflet which is movable relative to the support structure between an open configuration in which the leaflet permits blood flow through the aperture and a closed configuration in which the leaflet restricts blood flow through the aperture,
   wherein the aperture defines an axis and a lateral cross-section taken through the leaflet in a plane lateral to the axis defines an outwardly convex portion, an outwardly concave portion and a junction between the convex and concave portions,
   wherein the leaflet is attached to the support structure along first and second at least partially straight lines of attachment such that movement of the leaflet between the open and closed configurations results in the convex portion of the lateral cross-section pivoting about one of the first and second lines of attachment and the concave portion of the lateral cross-section pivoting about the other of the first and second lines of attachment, and
   wherein the leaflet is attached to the support structure along a base line of attachment which is adjacent to the aperture and which extends circumferentially at least part way around the aperture.

28. An artificial heart valve comprising a support structure defining an aperture for blood flow and a flexible leaflet which is movable relative to the support structure between an open configuration in which the leaflet permits blood flow through the aperture and a closed configuration in which the leaflet restricts blood flow through the aperture,
   wherein the aperture defines an axis and a lateral cross-section taken through the leaflet in a plane lateral to the axis defines an outwardly convex portion, an outwardly concave portion and a junction between the convex and concave portions,
   wherein the leaflet is attached to the support structure along first and second at least partially straight lines of attachment such that movement of the leaflet between the open and closed configurations results in the convex portion of the lateral cross-section pivoting about one of the first and second lines of attachment and the concave portion of the lateral cross-section pivoting about the other of the first and second lines of attachment, and
   wherein a length of the convex portion of the lateral cross-section comprises a greater proportion of a total length of the lateral cross-section in the open configuration than in the closed configuration.

29. An artificial heart valve comprising a support structure defining an aperture for blood flow and a flexible leaflet which is movable relative to the support structure between an open configuration in which the leaflet permits blood flow through the aperture and a closed configuration in which the leaflet restricts blood flow through the aperture,
   wherein the leaflet is attached to the support structure along first and second at least partially straight lines of attachment,
   wherein the leaflet is attached to the support structure along a base line of attachment which is adjacent to the aperture,
   wherein the leaflet comprises a free edge which extends opposite the base line of attachment and which extends between the first and second lines of attachment, the free edge being movable relative to the support structure,
   wherein the leaflet defines a co-aptation region which extends from the free edge to a boundary which is located between the free edge and the base line of attachment, the co-aptation region defining a plurality of generally identical lateral cross-sections,
   wherein the aperture defines an axis, a first lateral cross-section taken through the leaflet in a first plane lateral to the axis defines a single outwardly convex portion and a single outwardly concave portion, and a second lateral cross-section taken through the leaflet in a second plane lateral to the axis defines a single outwardly convex portion and a single outwardly concave portion,
   wherein the first and second lateral cross-sections are both located axially between the base line of attachment and the boundary of the co-aptation region such that the first lateral cross-section is closer to the base line of attachment that the second lateral cross-section,
   wherein the convex portion of the first lateral cross-section is longer than the convex portion of the second lateral cross-section and the concave portion of the first lateral cross-section is shorter than the concave portion of the second lateral cross-section, and
   wherein the leaflet is attached to the support structure along the first and second lines of attachment such that movement of the leaflet between the open and closed configurations results in the convex portions of the first and second lateral cross-sections pivoting about one of the first and second lines of attachment and the concave portions of the first and second later cross-sections pivoting about the other of the first and second lines of attachment.

30. An artificial heart valve comprising:
   a support structure comprising a generally annular base portion which defines an aperture for blood flow and which further defines a through hole extending through a wall thickness of the base portion; and
   a leaflet material integrally formed around the support structure so as to define a flexible leaflet which is movable relative to the support structure between an open configuration in which the leaflet permits blood flow through the aperture in a blood flow direction and a closed configuration which the leaflet restricts blood flow through the aperture in a direction opposite to the blood flow direction, wherein, when viewed on a longitudinal cross-section which is generally parallel to an axis defined by the aperture and which passes through the through hole, the leaflet material completely envelops the base portion, the leaflet material extends throng the through hole, and the flexible leaflet extends from the through hole.

31. An artificial heart valve according to claim 30, wherein, when viewed on the longitudinal cross-section, a curvature of a base region of the flexible leaflet adjacent to the through hole is continuous with a curvature of the portion of the leaflet material extending through the through hole.

32. An artificial heart valve according to claim 30, wherein the through hole is elongated or comprises a slit.

33. An artificial heart valve according to claim 30, wherein, when viewed on the longitudinal cross-section, the through hole extends in a direction which is angled between a radially inward direction and the direction of blood flow.

34. An artificial heart valve according to claim 30, wherein the base portion defines a plurality of through holes, each through hole extends through the wall thickness of the base portion, the leaflet material extends through two or more of the through holes, and the flexible leaflet extends from two or more of the through holes.

35. An artificial heart valve according to claim 30, wherein the support structure comprises at least one post portion extending from the base portion, the at least one post portion defining a through hole extending therethrough, and wherein, when viewed on a lateral cross-section which is generally lateral to the axis and which passes through the through hole defined by the at least one post portion of the support structure, the leaflet material completely envelops the at least one post portion, the leaflet material extends through the through hole defined by the at least one post portion, and the flexible leaflet extends from the through hole defined by the at least one post portion.

36. An artificial heart valve according to claim 30, wherein the leaflet material comprises at least one of a synthetic material, a polymer material, and polyurethane.

37. An artificial heart valve comprising:
a support structure comprising a generally annular base portion which defines an aperture for blood flow and at least one post portion extending from the base portion, the least one post portion defining a through hole which extends therethrough; and
a leaflet material integrally formed around the support structure so as to define a flexible leaflet which is movable relative to the support stricture between an open configuration in which the leaflet permits blood flow through the aperture in a blood flow direction and a closed configuration in which the leaflet restricts blood flow through the aperture in a direction opposite to the blood flow direction,
wherein, when viewed on a lateral cross-section which is generally lateral to an axis defined by the aperture and which passes through the through hole, the leaflet material completely envelops the at least one post portion, the leaflet material extends through the through hole, and the flexible leaflet extends from the through hole.

38. An artificial heart valve according to claim 37, wherein, when viewed on the lateral cross-section, curvature of a side region of the flexible leaflet adjacent to the through hole is continuous with curvature of the portion of the leaflet polymer material extending through the through hole.

39. An artificial heart valve according to claim 37, wherein the through hole is elongated or comprises a slit.

40. An artificial heart valve according to claim 37, wherein, when viewed on the lateral cross-section, the through hole extends in a direction which is angled with respect to a radially inward direction.

41. An artificial heart valve according to claim 37, wherein the at least one post portion defines a plurality of through holes extending therethrough, the leaflet material extends through two or more of the through holes, and the flexible leaflet extends from two or more of the through holes.

42. An artificial heart valve according to claim 37, wherein the base portion of the support structure defines a through hole extending through a wall thickness of the base portion and, when viewed on a longitudinal cross-section which is generally parallel to the axis and which passes through the through hole defined by the base portion, the leaflet material completely envelops the base portion, the leaflet material extends through the through hole defined by the base portion, and the flexible leaflet extends from the through hole defined by the base portion.

43. An artificial heart valve according to claim 37, wherein the leaflet material comprises at least one of a synthetic material, a polymer material, and polyurethane.

44. An artificial heart valve, comprising:
a support structure comprising a generally annular base portion which defines an aperture for blood flow and which further defines a through hole extending through a wall thickness of the base portion; and
a leaflet material integrally formed around the support structure so as to define a flexible leaflet which is movable relative to the support structure between an open configuration in which the leaflet permits blood flow through the aperture in a direction of blood flow and a closed configuration in which the leaflet restricts blood flow through the aperture in a direction opposite to the direction of blood flow,
wherein, when viewed on a longitudinal cross-section which is generally parallel to an axis defined by the aperture and which passes through the through hole, the through hole extends in a direction which is angled between a radially inward direction and the direction of blood flow, the leaflet material completely envelops the base portion, and the leaflet material extends through the through hole.

45. An artificial heart valve, comprising:
a support structure comprising a generally annular base portion which defines an aperture for blood flow and which further defines a through hole extending through a wall thickness of the base portion; and
a leaflet material integrally formed around the support structure so as to define a flexible leaflet which is movable relative to the support structure between an open configuration in which the leaflet permits blood flow through the aperture in a direction of blood flow and a closed configuration in which the leaflet restricts blood flow through the aperture in a direction opposite to the direction of blood flow,
wherein, when viewed on a longitudinal cross-section which is generally parallel to an axis defined by the aperture and which passes through the through hole, the leaflet material completely envelops the base portion, the leaflet material extends through the through hole, and a curvature of a base region of the flexible leaflet adjacent to the through hole is continuous with a curvature of the portion of the leaflet material extending through the through hole.

46. An artificial heart valve, comprising:

a support structure comprising a generally annular base portion which defines an aperture for blood flow and at least one post portion extending from the base portion, the at least one post portion defining a through hole which extends therethrough; and a leaflet material integrally formed around the support structure so as to define a flexible leaflet which is movable relative to the support structure between an open configuration in which the leaflet permits blood flow through the aperture in a direction of blood and a closed configuration in which the leaflet restricts blood flow through the aperture in a direction opposite to the direction of blood flow, wherein, when viewed on a lateral cross-section which is generally lateral to an axis defined by the aperture and which passes through the through hole, the through hole extends in a direction which is angled relative to a radially inward direction, the leaflet material completely envelops the at least one post portion, and the leaflet material extends through the through hole.

47. An artificial heart valve comprising, a support structure comprising a generally annular base portion which defines an aperture for blood flow and at least one post portion extending from the base portion, the at least one post portion defining a through hole which extends therethrough; and a leaflet material integrally formed around the support structure so as to define a flexible leaflet which is movable relative to the support structure between an open configuration in which the leaflet permits blood flow through the aperture in a direction of blood flow and a closed configuration in which the leaflet restricts blood flow through the aperture in a direction opposite to the direction of blood flow, wherein, when viewed on a lateral cross-section which is generally lateral to an axis defined by the aperture and which passes through the through hole, the leaflet material completely envelops the at least one post portion, the leaflet material extends through the through hole, and a curvature of a side region of the flexible leaflet adjacent to the through hole is continuous with a curvature of the portion of the leaflet material extending through the through hole.

\* \* \* \* \*